US005792743A

United States Patent [19]

Schachner

[11] Patent Number: 5,792,743
[45] Date of Patent: Aug. 11, 1998

[54] METHOD FOR PROMOTING NEURAL GROWTH COMPRISING ADMINISTERING A SOLUBLE NEURAL CELL ADHESION MOLECULE

[75] Inventor: Melitta Schachner, Zurich, Switzerland

[73] Assignee: Acorda Therapeutics, New York, N.Y.

[21] Appl. No.: 487,052

[22] Filed: Jun. 7, 1995

Related U.S. Application Data

[63] Continuation-in-part of Ser. No. 424,995, Apr. 19, 1995, abandoned.

[51] Int. Cl.$^6$ .................. A61K 38/16; C07K 14/435; C07K 14/475
[52] U.S. Cl. ............................... 514/2; 530/350
[58] Field of Search ................ 514/2; 530/350; 435/7.2

[56] References Cited

U.S. PATENT DOCUMENTS

| | | | |
|---|---|---|---|
| 4,508,715 | 4/1985 | Booth et al. | 514/280 |
| 4,955,892 | 9/1990 | Danilhoff et al. | 606/152 |
| 5,211,657 | 5/1993 | Yamada et al. | 623/1 |
| 5,277,966 | 1/1994 | Jessell et al. | 435/320.1 |
| 5,591,432 | 1/1997 | Bronson et al. | 424/130.1 |

FOREIGN PATENT DOCUMENTS

| | | |
|---|---|---|
| 572664 | 12/1993 | European Pat. Off. |
| WO 89/09600 | 10/1989 | WIPO |
| WO 94/14439 | 7/1994 | WIPO |

OTHER PUBLICATIONS

Kobayashi et al. (1995) Neuroscience Letters 188:191–194.
Rathjen et al. (1994) EMBO Journal 3:1–10, 1994.
Pigott et al. (1993) The Adhesion Molecule Factsbook, Academic Press Inc., San Diego, CA, pp. 6–7, 13–15., 112–113, 1993.
Ayad et al. (1994) The Extra Cellular Matrix Facts Book, Academic Press Inc. San Diego, CA pp. 6, 104, 111, 1994.
Doherty et al. (1995) Neuron 14:57–66.
Itoh, K. et al. (1995) Science 270:1369–72.
Wong et al. (1995) TINS 18:168–72.
Doherty et al. (1994) Curr. Opin. Neurobiol. 4:49–55.
Luthi et al. (1994) Nature 372:777–9.
Martini (1994) J. Neurocytol. 23:1–28.
Martini et al. (1994a) glia 10:70–74 (Abstract).
Schachner et al. (1994) Perspectives in Developm. Neurobiol. 2:33–41.
Toggas et al. (1994) Nature 367:188–193.
Appel et al. (1993) J. Neurosci., 13:4764–4775.
Horstkorte et al. (1993) J. Cell. Biol. 121:1409:1421 (Abstract).
Schwab et al. (1993) Ann. Rev. Neurosci. 15:565–595.
Atashi et al. (1992) Neuron 8:831–842.
Doherty et al. (1992) Curr. Opin. Neurobiol. 2:595–601.
Hynes (1992) Cell. 69:11–25.
Stuermer et al. (1992) J. Neurobiol. 23:537–550.
von Bohlen und Hallbach et al. (1992) Eur. J. Neurosci. 4:896–909.
Williams et al. (1992) J. Cell. Biol. 119:883–892.
Saad et al. (1991) J. Cell. Biol. 115:473–484 (Abstract).
Sarid (1991) J. Neurosci. 28:217–228.
Fawcett et al. (1990) Annu. Rev. Neurosci 13:43–60.
Kadmon et al. (1990a) J. Cell Biol. 110:193–208 (Abstract).
Kadmon et al. (1990b) J. Cell Biol. 110:209–218 (Abstract).
Landry et al. (1990) J. Neurosci. Res. 25:194–203.
Schachner (1990) Seminars in the Neurosciences 2:497–507.
Schuch et al. (1990) Neuron 3:13–20 (Abstract).
Smith et al. (1990) Dev. Biol. 138:377–390.
Wood et al. (1990) J. Neurosci 10:3635–3645 (Abstract).
Bartsch et al. (1989) J.Comp. Neurol 284:451–462.
Carlstedt et al. (1989) Brain Res. Bull. 22:93–102.
Bixby et al. (1988) J. Cell. Biol. 107:353–362.
Kalderon (1988) J. Neurosci Res. 21:501–512.
Moos et al. (1988) Nature 334:701–703.
Seilheimer et al. (1988) J. Cell. Biol. 107:341–351.
Bixby et al. (1987) Proc. Nat'l Acad. Sci. U.S.A. 84:2555–2559.
Chang et al. (1987) J. Cell. Biol. 104:355–362.
Lagenaur et al. (1987) Proc. Natl. Acad. Sci. USA 84:7753–7757.
Reik et al. (1987) Nature 328:248–251.
Sapienze et al. (1987) Nature 328:241–254.
Seilheimer et al. (1987) EMBO J. 6:1611–1616.
Tacke et al. (1987) Neurosci. Lett. 82:89–94.
Proudfoot (1986) Nature 322:562–565.
Smith et al. (1986) J. Comp. Neurol. 251:23–43.
Aguayo (1985) "Axonal regeneration from injured neurons in the adult mammalian central nervous system," In: Synaptic Plasticity (Cotman, C.W., ed.) New York, The Guilford Press, pp. 457–484.
Friedman et al. (1985) J. Neurosci. 5:1616–25.
Miller et al. (1985) Develop. Biol. 111:35–41.

(List continued on next page.)

*Primary Examiner*—Stephen Walsh
*Assistant Examiner*—Michael D. Pak
*Attorney, Agent, or Firm*—Klauber & Jackson

[57] ABSTRACT

The invention features a method for promoting neural growth in vivo in the mammalian central nervous system by administering a neural cell adhesion molecule which can overcome inhibitory molecular cues found on glial cells and myelin to promote neural growth. Also featured active fragments, cognates, congeners, mimics, analogs, secreting cells and soluble molecules thereof, as well as antibodies thereto, and DNA molecules, vectors and transformed cells capable of expressing them. The invention also includes transgenic mouse lines expressing a neural adhesion molecule in differentiated astrocytes, and cells and tissues derived therefrom. The expression of the neural adhesion molecule enhances neurite outgrowth on central nervous system tissue derived from these transgenic mice. The invention also features methods for enhancing neuronal outgrowth of CNS neurons, for enhancing memory and for increasing synaptic efficacy. Also featured are methods of testing drugs which modulate the effects of the neural adhesion molecule, and assay systems suitable for such methods.

3 Claims, 18 Drawing Sheets

OTHER PUBLICATIONS

Nieke et al. (1985) Differentiation 30:141–151.
Pollerberg et al. (1985) J. Cell. Biol. 101:1921–1929.
Lewis et al. (1984) Proc. Natl. Acad. Sci. 81:2743–2745.
Rathjen et al. (1984) EMBO J. 3:1–10.
Lindner et al. (1983) Nature 304:427–430.
Silver et al. (1982) J. Comp. Neurol. 210:10–29.
Silver et al. (1979) Develop. Biol. 68:175–90.
Eng et al. (1971) Brain Res. 28:351–354.
Kliot et al. "Induced regeneration of dorsal root fibres into the adult mammalian spinal cord," In: Current Issues in Neural Regeneration, New York, pp. 311–328.
Araujo et al. (1993) J. Neurochem. 61:899–910.
Jackowski (1995) British Journal of Neuro Surgery 9:303–317.

FIG.5A  FIG.5B  FIG.5C
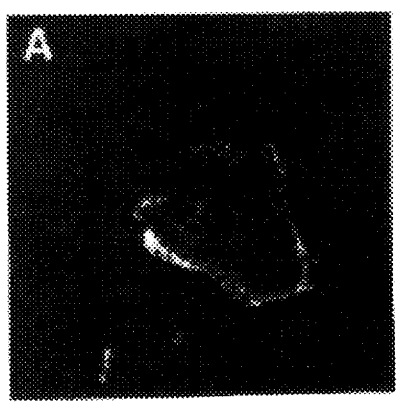 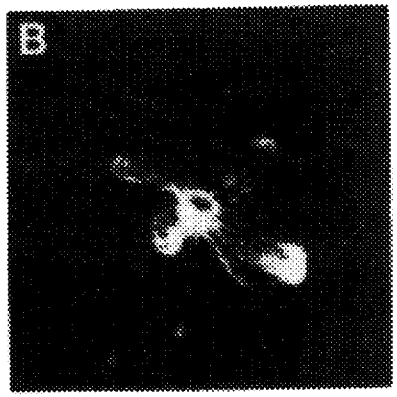 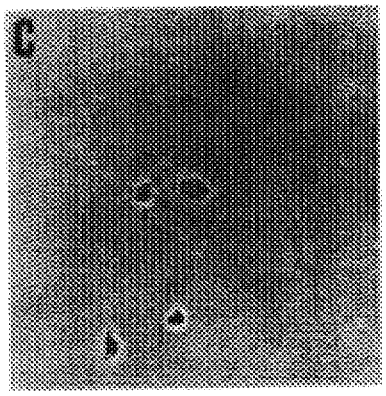
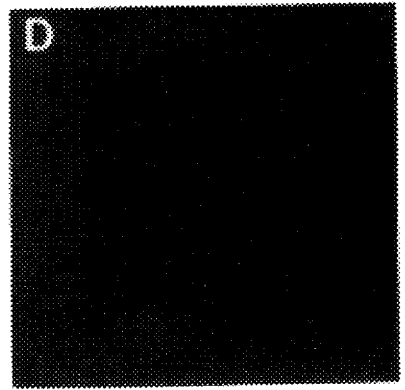 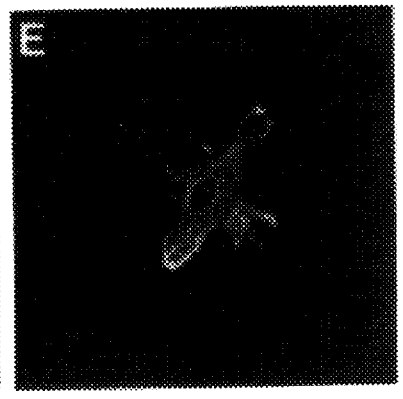 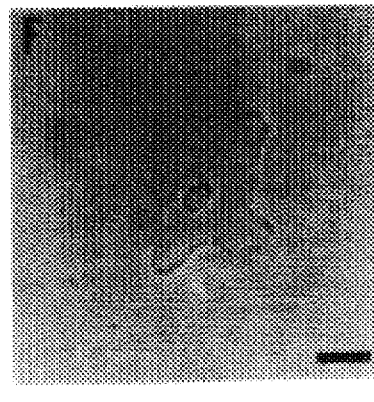
FIG.5D  FIG.5E  FIG.5F FIG.7A
FIG.7B
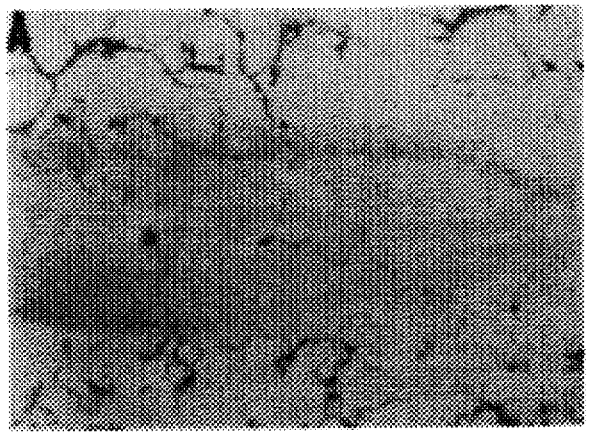
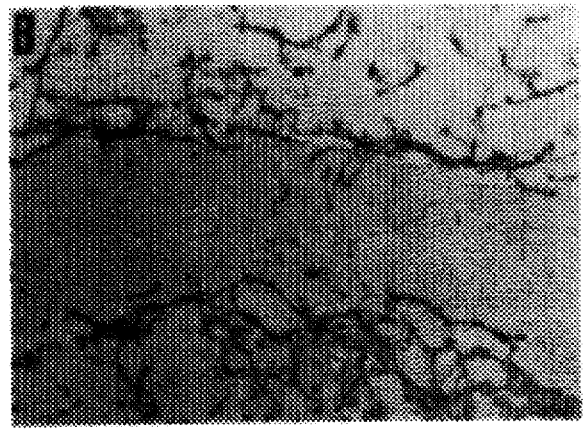
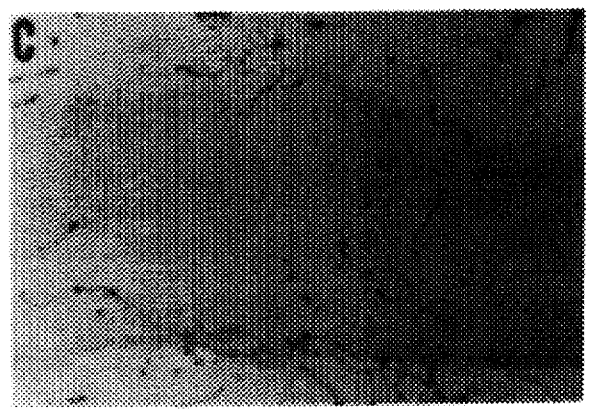
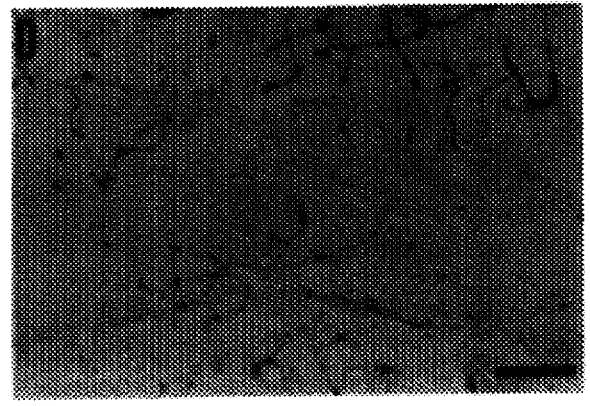
FIG.7C
FIG.7D

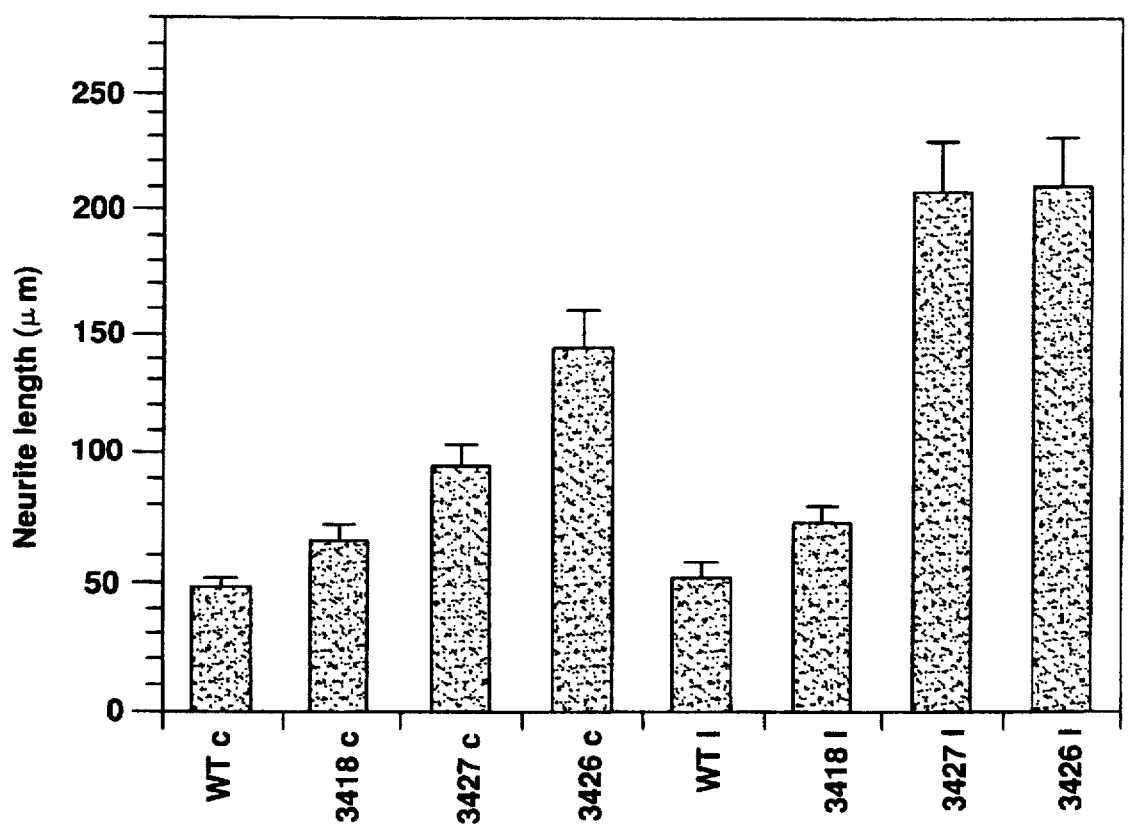

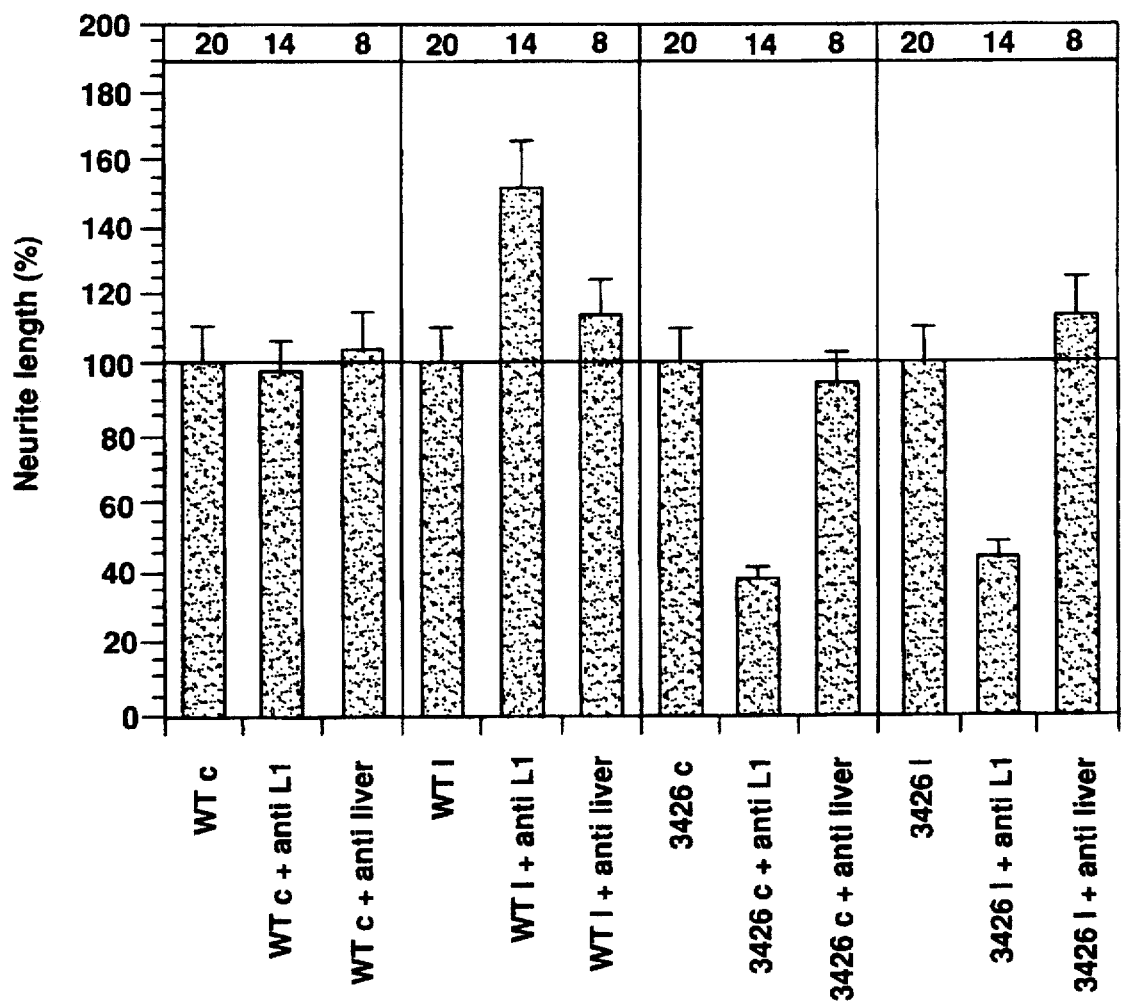

anti-L1, no TBS anti-L1, no TBS (whole cell recording)

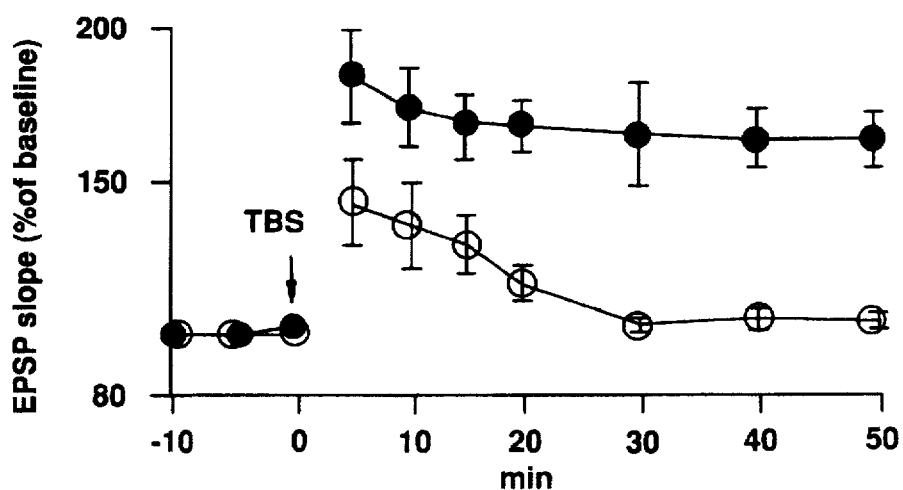
FIG.17A
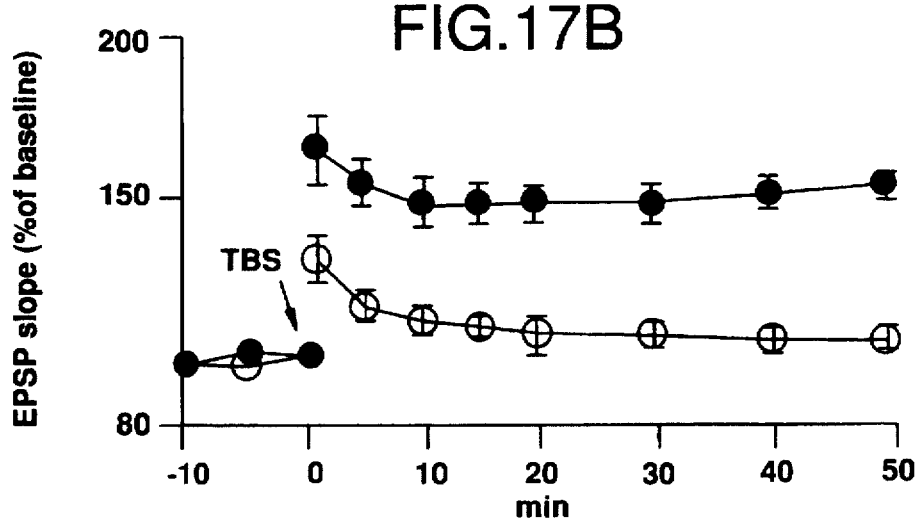
FIG.17B
FIG.17C
FIG.17D
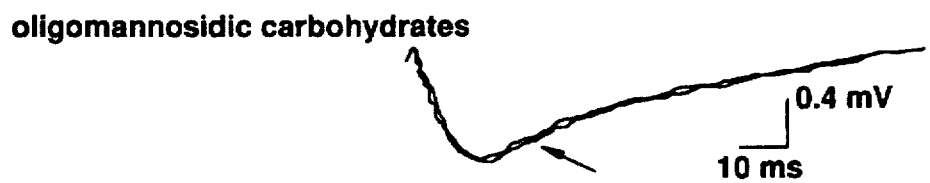

METHOD FOR PROMOTING NEURAL GROWTH COMPRISING ADMINISTERING A SOLUBLE NEURAL CELL ADHESION MOLECULE

CROSS REFERENCE TO RELATED APPLICATION

This application is a continuation-in-part application of U.S. Ser. No. 08/424,995, filed Apr. 19, 1995 now abandoned.

BACKGROUND OF THE INVENTION

1. Field of the Invention

This invention relates generally to the modulation of neural growth in the central nervous system, and more particularly to methods and associated agents, constructs and compositions for improving CNS neural growth. Specifically, the invention relates to the use of cellular adhesion molecules, and preferably neural cell adhesion molecules such as L1, to foster and improve such neural growth.

2. Description of the Related Art

The ability of neurons to extend neurites is of prime importance in establishing neuronal connections during development. It is also required during regeneration to re-establish connections destroyed as a result of a lesion.

Neurites elongate profusely during development both in the central and peripheral nervous systems of all animal species (Cajal (1928) Degeneration and regeneration in nervous system. Oxford University Press, London). This phenomenon pertains to axons and dendrites. However, in adults, axonal and dendritic regrowth in the central nervous system is increasingly lost with evolutionary progression.

In the peripheral nervous system, after infliction of a lesion, axons of all vertebrate species are able to regrow (Cajal (1928); Martini (1994) *J. Neurocytol.* 23:1–28). However, in mammals, neurite regrowth following damage is limited to neuritic sprouting. Regrowth of neuronal processes is, however, possible in lower vertebrate species (Stuermer et al. (1992) *J. Neurobiol.* 23:537–550). In contrast, in the central nervous system, most, if not all neurons of both higher and lower vertebrate adults possess the potential for neurite regrowth (Aguayo (1985) "Axonal regeneration from injured neurons in the adult mammalian central nervous system," In: Synaptic Plasticity (Cotman, C. W., ed.) New York, The Guilford Press, pp. 457–484.)

Glial cells are the decisive determinants for controlling axon regrowth. Mammalian glial cells are generally permissive for neurite outgrowth in the central nervous system during development (Silver et al. (1982) *J. Comp. Neurol.* 210:10–29; Miller et al. (1985) *Develop. Biol.* 111:35–41; Pollerberg et al. (1985) *J. Cell. Biol.* 101:1921–1929) and in the adult peripheral nervous system (Fawcett et al. (1990) *Annu. Rev. Neurosci* 13:43–60). Thus, upon infliction of a lesion, glial cells of the adult mammalian peripheral nervous system can revert to some extent to their earlier neurite outgrowth-promoting potential, allowing them to foster regeneration (Kalderon (1988) *J. Neurosci Res.* 21:501–512; Kliot et al. "Induced regeneration of dorsal root fibres into the adult mammalian spinal cord," In: *Current Issues in Neural Regeneration,* New York, pp. 311–328; Carlstedt et al. (1989) *Brain Res. Bull.* 22:93–102). Glial cells of the central nervous system of some lower vertebrates remain permissive for neurite regrowth in adulthood (Stuermer et al. (1992) *J. Neurobiol.* 23:537–550). In contrast, glial cells of the central nervous system of adult mammals are not conducive to neurite regrowth following lesions.

Several recognition molecules which act as molecular cues underlying promotion and/or inhibition of neurite growth have been identified (Martini (1996). Among the neurite outgrowth promoting recognition molecules, the neural cell adhesion molecule L1 plays a prominent role in mediating neurite outgrowth (Schachner (1990) *Seminars in the Neurosciences* 2:497–507). L1-dependent neurite outgrowth is mediated by homophilic interaction. L1 enhances neurite outgrowth on L1 expressing neurites and Schwann cells, and L1 transfected fibroblasts (Bixby et al. (1982) *Proc. Nat'l Acad. Sci. U.S.A.* 84:2555–2559; Chang et al. (1987) *J. Cell. Biol.* 104:355–362; Lagenaur et al. (1987) *Proc. Natl. Acad. Sci. USA* 84:7753–7757; Seilheimer et al. (1988) *J. Cell. Biol.* 107:341–351; Kadmon et al. (1990a) *J. Cell. Biol.* 110:193–208; Williams et al. (1992) *J. Cell. Biol.* 119:883–892). Expression of L1 is enhanced dramatically after cutting or crushing peripheral nerves of adult mice (Nieke et al. (1985) *Differentiation* 30:141–151; Martini et al. (1994a) *Glia* 10:70–74). Within two days L1 accumulates at sites of contact between neurons and Schwann cells being concentrated mainly at the cell surface of Schwann cells but not neurons (Martini et al. (1994a)). Furthermore, the homophilic binding ability of L1 is enhanced by molecular association with the neural cell adhesion molecule N-CAM, allowing binding to occur through homophilic assistance (Kadmon et al. (1990a); Kadmon et al. (1990b) *J. Cell Biol.* 110:209–218 and 110:193–208; Horstkorte et al. (1993) *J. Cell. Biol.* 121:1409–1421). Besides its neurite outgrowth promoting properties, L1 also participates in cell adhesion (Rathjen et al. (1984) *EMBO J.* 3:1–10; Kadmon et al. (1990b) *J. Cell. Biol.* 110:209–218; Appel et al. (1993) *J. Neurosci.,* 13:4764–4775), granule cell migration (Lindner et al. (1983) *Nature* 305:427–430) and myelination of axons (Wood et al. (1990) *J. Neurosci* 10:3635–3645).

L1 consists of six immunoglobulin-like domains and five fibronectin type III homologous repeats. L1 acts as a signal transducer, with the recognition process being a first step in a complex series of events leading to changes in steady state levels of intracellular messengers. The latter include inositol phosphates, $Ca^{2+}$, pH and cyclic nucleotides (Schuch et al. (1990) *Neuron* 3:13–20; von Bohlen und Hallbach et al. (1992) *Eur. J. Neurosci.* 4:896–909; Doherty et al. (1992) *Curr. Opin. Neurobiol.* 2:595–601) as well as changes in the activities of protein kinases such as protein kinase C and $pp60^{c-arc}$ (Schuch et al. (1990) *Neuron* 3:13–20; Atashi et al. (1992) *Neuron* 8:831–842). L1 is also associated with a casein type II kinase and another unidentified kinase which phosphorylates L1 (Sadoul et al. (1989) *J. Neurochem* 328:251–254). L1-mediated neurite outgrowth is sensitive to the blockage of L type $Ca^{2+}$ channels and to pertussis toxin. These findings indicate the importance of both $Ca^{2+}$ and G proteins in L1-mediated neurite outgrowth (Williams et al. (1992) *J. Cell. Biol.* 119:883–892). L1 is also present on proliferating, immature astrocytes in culture and neurite outgrowth is promoted on these cells far better than on differentiated, L1 immunonegative astrocytes (Saad et al. (1991) *J. Cell. Biol.* 115:473–484). In vivo, however, astrocytes have been found to express L1 at any of the developmental stages examined from embryonic day 13 until adulthood (Bartsch et al. (1989) *J. Comp. Neurol* 284:451–462; and unpublished data).

Given the capability of L1 to promote neurite outgrowth, it is pertinent to investigate whether astrocytic expression of L1 and other members of the immunoglobulin superfamily to which L1 belongs, may overcome potentially inhibitory molecular cues reported to be present on glial cells and myelin in the adult central nervous system (Schachner et al., *Perspectives in Developm. Neurobiol.* in Press; Schwab et al. (1993) *Ann. Rev. Neurosci.* 16:565–595). This is of particular relevance to the development of effective strategies for the treatment of debilitation caused by the malformation of, or injury to, neural tissues of the CNS, and it is toward such objectives that the present invention is directed.

SUMMARY OF THE INVENTION

In accordance with the present invention, an agent and corresponding methods are disclosed for the modulation of neural growth and particularly, such growth as can be promoted in the compartment of the central nervous system (CNS), and specifically, in myelinated nerve tissue. The agents of the present invention are notable in their ability to promote such neural growth in an environment that has been traditionally viewed as inhibitory to the growth promoting stimulus of known neurite outgrowth factors. Specifically, this inhibitory environment includes inhibitory molecular cues which are present on glial cells and myelin the central nervous system.

The agents of the present invention are broadly selected from a group of cell adhesion molecules, and more preferably neural cell adhesion molecules. Most preferably, the agents of the present invention are selected from the group of molecules belonging to the immunoglobulin superfamily, and particularly to those members that mediate $Ca^{2+}$-independent neuronal cell adhesion, of which L1, N-CAM and myelin-associated glycoprotein are particular members. Other cell adhesion molecules which may also influence CNS neural growth include laminin, fibronectin, N-cadherin, BSP-2 (mouse N-CAM), D-2, 224-1A6-A1, L1-CAM, NILE, Nr-CAM, TAG-1 (axonin-1), Ng-CAM and F3/F11.

The agents of the present invention also include fragments of cell adhesion molecules and cognate molecules, congeners and mimics thereof which modulate neurite growth in the CNS. In particular, the agents include molecules which contain structural motifs characteristic of extracellular matrix molecules, in particular the fibronectin type III homologous repeats and immunoglobulin-like domains. Preferably, these structural motifs include those structurally similar to fibronectin type III homologous repeats 1–2, and immunoglobulin-like domains I–II, III–IV and V–VI.

The invention extends to methods of promoting and enhancing neural regeneration in vivo, and to the corresponding genetic constructs, such as plasmids, vectors, transgenes, and the like, and to pharmaceutical compositions, all of which may be used to accomplish the objectives of such methods. More specifically, the agents of the present invention may be prepared as vectors or plasmids, and introduced into neural cells located at a site in the CNS where regeneration is needed, for example, by gene therapy techniques, to cause the expression of an agent of the present invention and to thereby promote the requisite neural growth. Another strategy contemplates the formulation of one or more of the appropriate agents in a composition that may likewise be directly delivered to a CNS site, as by parenteral administration. As certain of the agents, such as L1, have demonstrated homophilic binding, the administration of such a composition may serve the purpose of inhibiting rather than promoting neural growth. This effect may be desirable in particular instances where unwanted or uncontrolled growth may occur or is occurring, and therefore the invention extends to this use as well.

The invention also covers diagnostic applications, where for example, it is desirable to assess the potential for or actual development of CNS neural growth by the detection and measurement of the presence, amount or activity of one or more of the agents of the invention. Likewise, and as described hereinafter, the invention also extends to assays, including drug discovery assays, that capitalize on the activity of the agents of the present invention in the modulation of CNS neural growth. For example, prospective drugs may be tested for CNS neural growth modulation by means of an assay containing an agent of the invention, or a cell line or culture developed in conjunction herewith may serve as the assay system.

Briefly, the present invention also features transgenic mouse lines expressing a neural adhesion molecule in differentiated astrocytes, and cells and tissues derived therefrom. In particular, the neural adhesion molecule is L1. The astroglial L1 expression enhances neurite outgrowth on central nervous system tissue derived from these transgenic mice.

Also as discussed, the invention features methods for enhancing neuronal outgrowth of CNS neurons, for enhancing memory and for increasing synaptic efficacy, as measured by stabilization of long term potentiation, and other similarly useful methods. Also featured are methods of testing drugs and other manipulations which modulate the effects of the neural adhesion molecule, and assay systems suitable for such methods.

Accordingly, it is a principal object of the present invention to provide a transgenic mammal, the glial cells of which express an exogenous neural adhesion molecule.

A further object of the invention is to provide a cell culture containing the glial cells of the transgenic mammal.

Yet another object of the invention is to provide a cell culture system containing lesioned or unlesioned optic nerves or other parts of the nervous system of the transgenic mammal.

Still a further object of the invention is to provide a method for enhancing neuronal outgrowth of CNS neurons, which includes culturing the neurons on the glial cell culture system.

A further object of the invention is to provide a method for enhancing neuronal outgrowth of CNS neurons, which includes culturing the neurons on the optic nerve or other parts of the nervous system placed in the cell culture system.

A still further object of the invention is to provide a method for enhancing neuronal outgrowth of CNS neurons, which includes the secretion of neural adhesion molecule by implanted cells.

Another object of the invention is to provide a method for enhancing memory, which includes administering to the brain of a mammal in need of memory enhancement, an amount of the cells of the glial cell culture system effective to enhance the memory of the mammal.

Yet another object of the invention is to provide a method for enhancing memory, including administering to the brain of a mammal in need of memory enhancement, an amount of the cells of the optic nerve or other parts of the nervous system placed in the cell culture system effective to enhance the memory of the mammal.

A still further object of the invention is to provide a method for enhancing memory, including delivering to the glial cells of the brain of a mammal in need of such memory enhancement, a vector which allows for the expression of a neural adhesion molecule in the glial cells.

A further object of the invention is to provide a method for enhancing memory, which includes the secretion of neural adhesion molecule by implanted cells.

Another object of the invention is to provide a method for increasing synaptic efficacy in the CNS of a mammal in need of such an increase, including administering to the brain of the mammal, an amount of the cells of the glial cell culture system effective to increase synaptic efficacy in the brain of the mammal.

Yet a further object of the invention is to provide a method for increasing synaptic efficacy in the CNS of a mammal in need of such an increase, including administering to the brain of the mammal, an amount of the cells of the optic nerve or other parts of the nervous system placed in the cell culture system effective to increase synaptic efficacy in the brain of the mammal.

A still further object is to provide a method for increasing synaptic efficacy in the CNS of a mammal in need of such an increase, which includes delivering to the glial cells of the brain of a mammal in need of such enhancement, a vector which allows for the expression of a neural adhesion molecule in the glial cells.

A further object of the invention is to provide a method for increasing synaptic efficacy, which includes the secretion of neural adhesion molecule by implanted cells.

Another object of the invention is to provide a method of testing the ability of a drug or other entity to modulate the activity of a neural adhesion molecule, which includes adding CNS neurons to the glial cell culture system; adding the drug under test to the cell culture system; measuring the neuronal outgrowth of the CNS neurons; and correlating a difference in the level of neuronal outgrowth of cells in the presence of the drug relative to a control culture to which no drug is added to the ability of the drug to modulate the activity of the neural adhesion molecule.

Another object of the invention is to provide a method of testing the ability of a drug or other entity to modulate the activity of a neural adhesion molecule which includes adding CNS neurons to the optic nerve or other parts of the nervous system cell culture system; adding the drug under test to the cell culture system; measuring the neuronal outgrowth of the CNS neurons; and correlating a difference in the level of neuronal outgrowth of cells in the presence of the drug relative to a control culture to which no drug is added to the ability of the drug to modulate the activity of the neural adhesion molecule.

Yet another object of the invention is to provide an assay system for screening drugs and other agents for ability to modulate the production of a neural adhesion molecule, which includes the glial cell culture system; and CNS neurons added to the cell culture system.

A further object of the invention is to provide an assay system for screening drugs and other agents for ability to modulate the production of a neural adhesion molecule, which includes culturing the glial cell culture system inoculated with a drug or agent; adding CNS neurons to the cell culture system; and examining neuronal outgrowth to determine the effect of the drug thereon.

Yet another object of the invention is to provide an assay system for screening drugs and other agents for ability to modulate the production of a neural adhesion molecule, which includes culturing the optic nerve or other parts of the nervous system in the cell culture system inoculated with a drug or agent; adding CNS neurons to the cell culture system; and examining neuronal outgrowth to determine the effect of the drug thereon.

Another object of the invention is to provide an assay system for screening drugs and other agents for ability to modulate the production of a neural adhesion molecule, which includes inoculating a culture of CNS neurons with a drug or agent; adding a soluble neural adhesion molecule; and examining neuronal outgrowth to determine the effect of the drug thereon.

Other objects and advantages will become apparent to those skilled in the art from a review of the ensuing detailed description taken with reference to the following illustrative drawings.

BRIEF DESCRIPTION OF THE DRAWINGS

FIG. 5 depicts the double immunofluorescence microscopic localization of L1 (A and D) and GFAP (1 and E) in cultured astrocytes from transgenic animals of line 3426 (A, B and C) and wild type animals (D, E and F). Note that only the cells from transgenic animals express L1, whereas astrocytes from wild type animals are L1 negative. Scale bar in F:30 µm (for A to F).

FIG. 7 depicts examples of neurite outgrowth from mouse cerebellar neurons cultured on cryostat sections of optic nerves from wild type (A and B) and transgenic (C and D) animals (line 3426). A and C represent unlesioned optic nerves, B and D represent lesioned optic nerves. Scale bar in D:50 μm (for A to D).

FIG. 8 depicts and compares neurite lengths of cerebellar neurons maintained on cryostat sections of unlesioned (c) and lesioned (1) optic nerves (28 days after the lesion) from wild type (WT) and transgenic animals (lines 3426, 3427 and 3418). Note that the length of neurites on sections from transgenic animals is greater than on sections from wild type animals. In transgenic lines neurites are always longer on lesioned than on unlesioned nerves, whereas neurite lengths on unlesioned and lesioned nerves of wild type animals do not show a significant difference. Note that the neurite length correlates positively with the levels of L1 expression in different transgenic lines (see also Western blot data). Mean values ± standard error of the mean from one representative experiment (out of 12) are shown.

FIG. 9 is a graph measuring neurite lengths of cerebellar neurons maintained on cryostat sections of unlesioned (c) and lesioned (1) optic nerves (28 days after the lesion) from wild type (WT) and transgenic animals without and after pre-incubation of sections with affinity purified polyclonal antibodies against L1 (anti L1) and mouse liver membranes (anti liver). Neurite lengths on nerves without pre-incubation with any antibody were taken as 100% and neurite lengths on sections of the same nerves obtained after antibody treatment were expressed in relation to this value. A significant reduction (60%) of neurite length by L1 antibodies was found on cryostat sections from transgenic animals. Numbers on the top represent the total number of nerves measured for each value. Mean values ± standard error of the mean are from at least four independent experiments carried out in duplicate.

FIG. 17 graphically depicts the influence of L1 antibodies and oligomannosidic carbohydrates on previously established LTP and on MNDA receptor-mediated synaptic transmission. a, Time-course of the EPSP initial slope before and after TBS in the presence of L1 antibodies applied either throughout the experiment (6.2 mg/ml; ○) or starting 10 minutes after TBS (6.2 mg/ml; ●). b, time-course of the EPSP initial slope before and after TBS in the presence of oligomannosidic carbohydrates applied either throughout the experiment (100 µM; ○) or starting 20 minutes after TBS (100 µM; ●). c, Averaged (n=4) NMDA receptor-dependent EPSP's recorded in the presence of CNQX (30 µM) before and after 30 minutes (arrow) application of L1 antibodies. d, Averaged (n=4) NMDA receptor-dependent EPSP's recorded in the presence of CNQX (10 µM) before and after (arrow) 60 minutes of application of oligomannosidic carbohydrates. Results in a and b are expressed as means ± S.E.M. of the EPSP initial slope in percent of the baseline values recorded during the 20 min. before TBS (n=5 slices from at least 3 animals).

DETAILED DESCRIPTION OF THE PREFERRED EMBODIMENTS OF THE INVENTION

Figure 1:
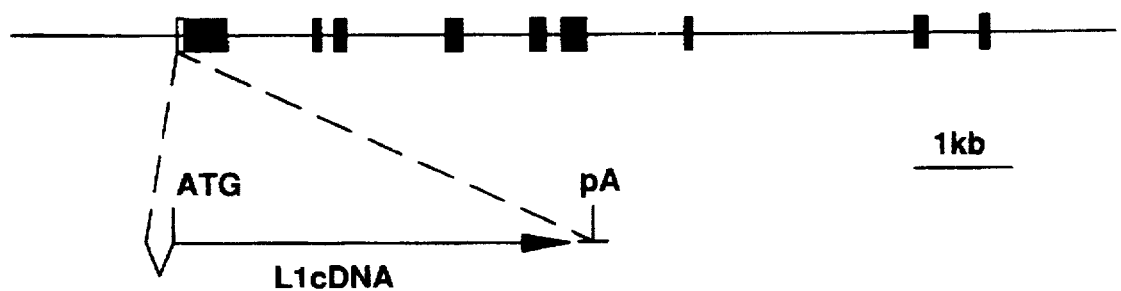
FIG. 1 depicts the map of the GFAP-L1 chimeric transgene. A 4.05 kb mouse L1 CDNA was inserted into exon 1 of a modified GFAP gene using Not I linkers. In this construct, the L1 cDNA is preceded 5' by an SV40 late gene splice (V) and followed 3' by an SV40 polyadenylation signal (pA). The locations of the L1 ATG and the polyadenylation signal are indicated. Exons are shown as boxes.

More particularly, the present invention relates to the use of certain agents identified herein as "CNS neural growth modulators" (CNGMs), and particularly to a class of neural cell adhesion molecules as defined herein, to promote neurite outgrowth in the central nervous system (CNS). In general, neurons in the adult central nervous system have been considered incapable of regrowth, due to inhibitory molecular cues present on glial cells. The agents and methods of the present invention can be used to overcome this inhibition and promote CNS neurite outgrowth.

The agents of the invention include and may be selected from any cell adhesion molecule which is capable of modulating or promoting CNS neurite outgrowth, and particularly to molecules belonging to the immunoglobulin superfamily. More particularly, the molecules are selected from the members of the immunoglobulin superfamily which mediate $Ca^{2+}$-independent neuronal cell adhesion, including L1, N-CAM and myelin-associated glycoprotein. The invention also contemplates fragments of these molecules, and analogs, cognates, congeners and mimics of these molecules which have neurite-promoting activity. Particularly preferable structural motifs for these fragments and analogs include domains similar to the fibronectin type III homologous repeats (particularly repeats 1–2) and immunoglobulin-like domains (particularly domains I–II, III–IV and V–VI).

The present invention relates in one aspect to the ectopic expression of CNS neural growth modulators (CNGMs) or neural cell adhesion molecules on differentiated astrocytes in vivo. These molecules have been found to enhance neurite outgrowth on monolayer cultures of such astrocytes and cryostat sections of unlesioned and lesioned adult mouse optic nerves, and also in vivo, in optic nerve crush experiments in transgenic animals. The increased neurite outgrowth-promoting capacity is proportional to the level of ectopic CNGM expression. This is demonstrated by comparisons of the distinct transgenic lines of the invention, which express different basal levels of transgenic-encoded CNGM, and by correlations following increased CNGM expression after a lesion of the optic nerve.

It should be appreciated that although optic nerves, both lesioned and unlesioned, are suitable for use with the present invention, that any part of the nervous system can likewise be used, including portions of the brain and spinal cord.

Neurite outgrowth is dependent on the levels of CNGM expression by astrocytes, demonstrating the specific effect exerted by CNGM in promoting neurite outgrowth in the transgenic animal. Inhibition of neurite outgrowth by polyclonal CNGM antibodies, but not by antibodies to mouse liver membranes, further supports this specificity, in particular, since both antibodies react well with the cell surfaces of neurons and astrocytes of transgenic animals.

In a preferred embodiment, the CNGM is L1. L1's biological effects can be inhibited by L1 antibodies, which indicates that L1 is homophilically active in a trans configuration at the cell surface of transgenic astrocytes. Furthermore, L1 species-specific antibodies that do not react with chicken dorsal root ganglion neurons inhibit neurite outgrowth of this neuronal cell type on transgenic astrocytes. These findings unequivocally identify L1 as a trans-acting active molecule and show that ectopic expression of L1 by glial cells that normally lack L1 expression significantly enhances neurite outgrowth in vitro.

The transgene-mediated enhancement of neurite outgrowth on glial cells that do not normally express L1 in vivo indicates that glial cells of the adult mammalian central nervous system can be made more conducive to neurite outgrowth. The loss of neurite outgrowth-promoting glia-derived molecules with maturation (Smith et al. (1986) J. Comp. Neurol. 251:23–43; Smith et al. (1990) Dev. Biol. 138:377–390) therefore appears to be compensated for by expression of a recognition molecule that is normally highly expressed by glial cells in the adult mammalian peripheral nervous system (Niecke et al. (1985); Bixby et al. (1988) J. Cell. Biol. 107:353–362; Seilheimer et al. (1988) [<m]ditJ. Cell. Biol. 107:341–351).

The phenotype of adult astrocytes from the present transgenic lines may be modified towards the more Schwann cell-related capacity of reexpressing L1 after infliction of a lesion. An increase in L1 expression by Schwann cells is likely mediated by neurotrophins upregulated after damage by autocrine mechanisms (Seilheimer et al. (1987), EMBO J. 6:1611–1616). Similarly, L1 expression by astrocytes in culture can be upregulated by TGF-βand NGF (Saad et al. (1991)). By generating mice with a GFAP-L1 transgene, the inability of mature astrocytes to respond to neural injury is overcome with an upregulation of the neurite outgrowth promoting molecule L1. The expression of L1 may be particularly beneficial for neurite outgrowth in myelinated tracts of the central nervous system which normally contain several molecules that are neurite outgrowth inhibiting (Schachner et al., Perspectives in Developm. Neurobiol. in Press; Schwab et al. (1995) Ann. Rev. Neurosci. 16:565–595).

The present invention demonstrates that the inhibitory action of astroglial and oligodendroglial cells may be overcome, at least in part, by the neurite outgrowth promoting properties of the agents defined herein, and as particularly illustrated by the activity of ectopically expressed L1. Expression of L1 by astrocytes seems also to compensate for inhibitory effects exerted by oligodendrocytes. Permissive and non-permissive molecular cues therefore may not have to be localized on the same cell type for neurite outgrowth to occur. Instead, such molecular cues might be partitioned among different cell types. The cellular and molecular manipulation of L1 and other neurite outgrowth promoting molecules may therefore allow enhancement of the regenerative capacity of the adult mammalian central nervous system following injury or disease.

As indicated earlier, the present invention extends to the promotion of neural growth in the CNS, including such growth as is desired to regenerate structures lost due to injury or illness, as well as those structures and tissues exhibiting incomplete or immature formation. The agents of the invention also exhibit a neuroprotective or neuropreservative effect as illustrated later on herein, and for example, could be administered to inhibit or counteract neural degeneration or loss of variable etiology.

The invention accordingly extends to constructs and compositions containing or delivering the agents of present invention, whether by the promotion of the expression of certain agents via gene therapy or the like, or by the exogenous administration of the agents where appropriate and beneficial, in pharmaceutical compositions to treat injured or diseased CNS structures. In this latter connection, it is contemplated that certain of the agents are able to exert a growth promoting effect when so administered, although it is recognized that members of the presently identified group, such as L1 and N-CAM appear to bind homophilically and may therefore prove more beneficial when delivered by means of expression. The invention is intended to extend to both routes and protocols where feasible.

It should also be appreciated that the present invention relates to the use of CNGM-secreting cells for the modulation of neural outgrowth, regeneration, and neural survival in the CNS. As such, certain soluble CNGMs and fragments thereof, and cognate molecules thereof are also within the invention.

Therefore, if appearing herein, the following terms shall have the definitions set out below.

The terms "agent", "CNS neural growth modulator", "CNGM", "neural recognition molecule", "recognition factor", "recognition factor protein(s)", "neural adhesion molecule", and any variants not specifically listed, may be used herein interchangeably, and as used throughout the present application and claims refer to proteinaceous material including single or multiple proteins, and extends to those proteins having the amino acid sequence previously described and the profile of activities set forth herein and in the Claims. The foregoing terms also include active fragments of such proteins, cognates, congeners, mimics and analogs, including small molecules that behave similarly to said agents.

Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "CNS neural growth modulator",  "CNGM", "neural recognition factor", "recognition factor", "recognition factor protein(s)", and "neural adhesion molecule" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to probes, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid.

With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In one aspect, the present invention relates to transgenic animals which express a CNGM or neural recognition molecule, in particular L1, and preferably in astrocytes. These animals have increased capability for neural outgrowth in the central nervous system.

The invention also includes an assay system for the screening of potential drugs effective to modulate neural outgrowth of target mammalian cells by interrupting or potentiating the CNGM's neural recognition activity. By "neural recognition activity" or "neural adhesion activity" is meant any biological effect which is a result of the CNGM's binding to another molecule, including intracellular effects on second messengers. In one instance, the test drug could be administered either to a cellular sample with the ligand that activates the CNS neural growth modulator, or a transgenic animal expressing the CNS neural growth modulator, to determine its effect upon the binding activity of the modulator to any chemical sample, or to the test drug, by comparison with a control. Identifying characteristics of at least one of the present CNS neural growth modulators, in particular L1, is its participation in changes in steady state levels of intracellular messengers, including $Ca^{2+}$, pH, and cyclic nucleotides, as well as changes in the activities of protein kinases such as protein kinase C, $pp60^{c-src}$, a casein type II kinase and another kinase known to phosphorylate L1.

The assay system could more importantly be adapted to identify drugs or other entities that are capable of binding to the CNGMs or proteins, either in the cytoplasm or in the nucleus, thereby inhibiting or potentiating transcriptional activity. Such assay would be useful in the development of drugs that would be specific to particular cellular activity, such as neural outgrowth or increase in synaptic efficacy, or that would potentiate such activity, in time or in level of activity. For example, such drugs might be used to modulate neural outgrowth in response to injury, or to treat other pathologies, as for example, in treating neurodegenerative diseases such as Parkinson's Disease, ALS, Huntington's Disease and Alzheimer's Disease.

In yet a further embodiment, the invention contemplates agonists and antagonists of the activity of a CNS neural growth modulator. In particular, an agent or molecule that inhibits the ability of neurons to recognize a CNGM such as L1 can be used to block neural outgrowth, where such outgrowth is contraindicated, and as described earlier, a pharmaceutical composition containing such an agent may be administered directly to the target site. In another embodiment, an agonist can be a peptide having the sequence of a portion of an L1 domain particularly that between fibronectin type III homologous repeats 2 and 3, or an antibody to that region. Either of these molecules may potentially be used where a particular CNGM such as L1 has the ability to undergo homophilic binding (i.e., L1 can bind to itself, and therefore both antibodies to L1 and fragments of L1 itself are capable of binding to L1).

One of the diagnostic utilities of the present invention extends to the use of the present CNGMs in assays to screen for protein kinase inhibitors. Because the activity of the CNGMs described herein are phosphorylated, they can and presumably are dephosphorylated by specific phosphatases. Blocking of the specific kinase or phosphatase is therefore an avenue of pharmacological intervention that would modulate the activity of these neural recognition proteins.

The present invention likewise extends to the development of antibodies against the CNGMs, including naturally raised and recombinantly prepared antibodies. For example, the antibodies could be used to screen expression libraries to obtain the gene or genes that encode the CNGMs. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating neural outgrowth.

In particular, antibodies against CNS neural growth modulators can be selected and are included within the scope of the present invention for their particular ability in binding to the protein. Thus, activity of the neural growth modulators or of the specific polypeptides believed to be causally connected thereto may therefore be followed directly by the assay techniques discussed later on, through the use of an appropriately labeled quantity of the neural growth modulator or antibodies or analogs thereof.

Thus, the CNGMs, their analogs, and any antagonists or antibodies that may be raised thereto, are capable of use in connection with various diagnostic techniques, including immunoassays, such as a radioimmunoassay, using for example, an antibody to the CNGM that has been labeled by either radioactive addition, reduction with sodium borohydride, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against the CNGMs may be selected and appropriately employed in the exemplary assay protocol, for the purpose of following protein material as described above.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the neural growth modulators, or to identify drugs or other agents that may mimic or block their activity. The system or test kit may comprise a labeled component prepared by one of the radioactive and/or enzymatic techniques discussed herein, coupling a label to the neural growth modulators, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the CNS neural growth modulator(s), its (or their) subunits, or active fragments thereof, or upon agents or other drugs determined to possess the same activity. A first therapeutic method is associated with the promotion of CNS neural growth resulting from the presence and activity of the CNGM, its active fragments, analogs, cognates, congeners or mimics, and comprises administering an agent capable of modulating the production and/or activity of the CNGM, in an amount effective to promote CNS development, regrowth or rehabilitation in the host. Conversely, drugs or other neutralizing binding partners to the CNGM or proteins may be administered to inhibit or prevent undesired neural outgrowth. Also, the modulation of the action of specific kinases and phosphatases involved in the phosphorylation and dephosphorylation of CNGMs or proteins presents a method for modulating the activity of the modulator or protein that would concomitantly potentiate therapies based on CNGM/protein activation.

More specifically, the therapeutic method generally referred to herein could include the method for the treatment of various pathologies or other cellular dysfunctions and derangements by the administration of pharmaceutical compositions that may comprise effective inhibitors or enhancers of the activity of the CNS neural growth modulator or its subunits, or other equally effective drugs developed for instance by a drug screening assay prepared and used in accordance with a further aspect of the present invention. For example, drugs or other binding partners to the CNS neural growth modulator or proteins may be administered to inhibit or potentiate binding and second messenger activity.

The following examples are presented in order to more fully illustrate the preferred embodiments of the invention. They should in no way be construed, however, as limiting the broad scope of the invention.

EXAMPLE 1

GFAP-L1 transgene and production of transgenic mice

Glial fibrillary acidic protein (GFAP. Eng et al. (1971) *Brain Res.* 28:351-354) is expressed predominately by astrocytes at late stages in the development of the mouse central nervous system (Landry et al. (1990) *J. Neurosci. Res.* 25:194-203). Therefore regulatory sequences of the GFAP gene were used to direct the expression of the neural cell adhesion molecule L1 to mature astrocytes of transgenic mice. The GFAP-L1 transgene (FIG. 1) encodes only the neural cell adhesion molecule L1 since the ATG of the GFAP gene was mutated and the L1 coding sequence is followed 3' by a translational stop and a polyadenylation signal (Toggas et al. (1994) *Nature* 367:188-193). This construct was used to establish three different lines of transgenic mice, designated 3418, 3426 and 3427.

The mouse L1 cDNA (Moos et al. (1988) *Nature* 334:701-703) was inserted into exon 1 of the murine glial fibrillary acidic protein (GFAP) gene modified as described previously (Toggas et al. (1994) *Nature* 367:188-193). The 4.05 kb mouse L1 cDNA containing the entire coding sequence of the protein and 250 3' non-translated nucleotides was fused with the modified GFAP-L1 transgene.

The 14.5 kb GFAP-L1 transgene was excised from a modified cloning vector by digestion with Sfi I, followed by electrophoresis and electroelution from an agarose gel. Purified DNA was diluted to a final concentration of 2 μg/ml in $T_5E_{0.1}$ (5 mM Tris-HCl, pH 7.4, 0.1 mM EDTA). Approximately 2 pl of diluted DNA were microinjected into the male pronucleus of fertilized eggs derived from CB6F1 females (superovulated) mated to C57B1/6J males. Eggs surviving the micromanipulation were transferred into oviducts of pseudo-pregnant foster mothers following described methods (Hogan et al. (1986) *Manipulating Mouse Embryo*, Cold Springs Harbor Laboratory, New York).

EXAMPLE 2

Southern blot analysis

Mice were analyzed for the integration of the transgene into the mouse genome by Southern blot analysis of genomic DNA isolated from tail biopsies (Southern (1975) *J. Mol. Biol.* 98:503–517). Transgenic founder mice were mated and pups screened in the same manner to establish transgenic lines. Ten μg samples of DNA were digested with either Bam HI or with Eco RI and Xba I followed by electrophoretic separation on a 0.7% agarose gel and transfer to Hybond N+ membrane (Amersham) under alkaline conditions. A 3.3 kb Eco RI-fragment of the L1 cDNA or a 330 bp Hind III fragment of SV40 late splice and polyadenylation site purified from A1.5 plasmid (Maxwell et al. (1989) *Biotechniques* 7:276–280) were labelled with $^{32}$ πα-CTP by random priming (Boehringer Mannheim) for use as probes. Prehybridization was performed at 65° C. for one hour in 5×SSPE, 5×Denhardt's solution, 0.5% (w/v) SDS and 0.1 mg/ml sonicated non-homologous DNA. Hybridization was performed overnight. Final stringency wash conditions for all Southern blots were 0.1×SSPE and 0.1% SDS (w/v) at 65° C.

EXAMPLE 3
Northern blot analysis

Anaesthetized adult mice (12-weeks-old) were sacrificed by a lethal dose of chloralhydrate and brains were removed and immediately frozen in liquid nitrogen. Total cellular RNA was isolated by pulverizing the tissue in liquid nitrogen. Four molar guanidinium thiocyanate was added to the pulverized tissue. Isolation of total RNA was performed as described (Chomczynski et al. (1987) *Anal. Biochem.* 162:156–159; Pagliusi et al. (1989) *AMOG. J. Neurosci. Res.* 22:113–119). RNA yields were estimated from absorbance at 260 nm. Ten μg of the RNA were fractionated on 1% agarose-formaldehyde gels for Northern blot analysis (Thomas (1980) *Proc. Natl. Acad. Sci. USA* 77:201–205).

Randomly primed L1 cDNA probes were used to simultaneously detect the endogenous L1 mRNA of 6 kb (Tacke et al. (1987) *Neurosci. Lett.* 82:89–94) and the transgene-derived L1 mRNA of 4.2 kb. Densitometric analysis of Northern blots was performed on scanned images (Arcus scanner, Agfa-Gavaert) of the original films using the Image Program (NIH, Research Services Branch, NIMH).

Figure 2:
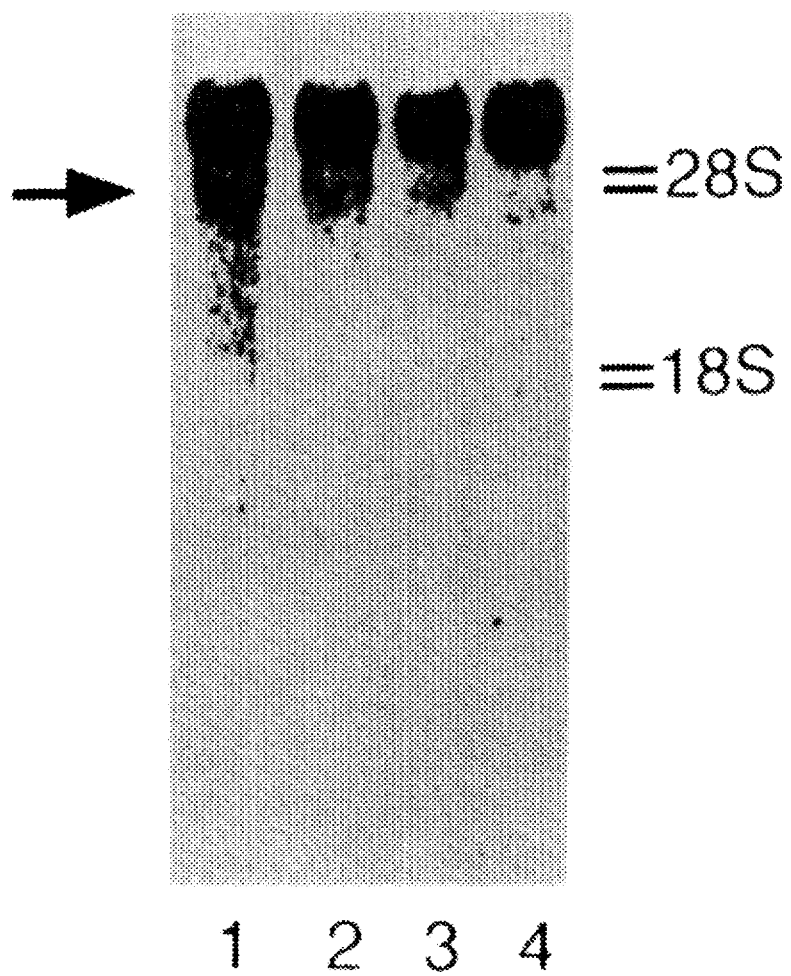
FIG. 2 depicts a Northern blot analysis of brain RNA from different transgenic lines. 10 µg of total RNA of whole adult brain was loaded in each lane and probed with mouse L1 CDNA. Exposure time was 3 days. Lanes 1–3, brains from different transgenic offspring (lane 1: line 3426; lane 2: line 3427; lane 3: line 3418; lane 4, brain from non-transgenic control). Note that the level of transgenic L1 mRNA (arrow) is different in the three transgenic lines, with levels being highest in line 3426, intermediate in line 3427 and lowest in line 3418. The position of 28S and 18S rRNA is shown on the right margin.

Northern blot analysis of total RNA from whole brains of the transgenic animals revealed L1 transcripts of a size (4.2 kb) expected for transgene-derived mRNA (FIG. 2.). These transcripts are clearly distinct from the endogenous L1 mRNA which is 6 kb and derived from postmitotic neurons. Densitometric analysis revealed that the levels of transgene-derived L1 mRNA were 34%, 13% and 8% in lines 3426, 3427 and 3418, respectively, as compared to the levels of endogenous L1 mRNA (rated 100%).

EXAMPLE 4
Animals

For cultures on cryostat sections, immunocytochemistry and in situ hybridization experiments, control animals were taken from stocks of age-matched normal C57b1/6J mice or non-transgenic littermates. For isolation of small cerebellar neurons and for preparation of astrocyte cultures six-day-old ICR non-transgenic pups were used. Dorsal root ganglion (DRG) neurons were prepared from eight-day-old chick embryos.

EXAMPLE 5
In situ hybridization

To verify that astrocytes of transgenic animals expressed L1 in vivo, optic nerves were analyzed by in situ hybridization. The optic nerve was chosen since it contains only glial cells and is free of neuronal cell bodies. Astrocytes in vivo normally lack expression of L1 at any developmental stage (unpublished data).

For detection of L1 mRNA in cryostat sections of fresh-frozen brain sections, digoxigenin-labelled cRNA was generated by in vitro transcription (Dörries et al. (1993) *Histochemistry* 99:251–262). The sequence encoding the extracellular part of L1 (Moos et al. (1988) was subcloned into the pBluescript KS+ (Stratagene) vector. Anti-sense and sense cRNA probes were generated by transcribing the L1 insert after linearization of the resulting plasmid with Xho I or Xba I, using the T7 and T3 promoters, respectively. For generation of GFAP cRNA probes, a 1.2 kb fragment of GFAP cDNA (Lewis et al. (1984) *Proc. Natl. Acad. Sci.* 81:2743–2745; kindly provided by Dr. N. J. Cowan) encoding the N-terminus of the protein was subcloned into the pBluescript KS+ vector. Anti-sense and sense cRNA probes were generated by transcribing the resulting plasmid, linearized with Eco RI and Xho I, from the T3 and T7 promoters, respectively. To improve tissue penetration, anti-sense and sense probes were sized under alkaline hydrolysis conditions to obtain an average fragment length of about 300 nucleotides. In situ hybridization on sections of optic nerves prepared from adult (12-weeks-old) animals was performed as described by elsewhere (Dörries et al. (1993); Bartsch et al., *J. Neurosci.*, in press).

Figure 3A:
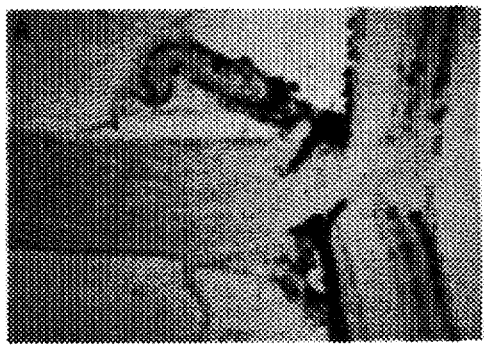
FIG. 3 depicts the localization of L1 mRNA in adult unlesioned (A, C and E) and lesioned (15 days after the lesion, B and D) optic nerves from non-transgenic (A, B and E) and transgenic mice (C and D) of line 3426 by in situ hybridization. In wild type animals, L1 mRNA is detectable only in neuronal cells of the retina but not in the glial cells of the optic nerve (A and B). In transgenic animals, cells containing L1 transcripts are visible in the optic nerve (C and D). The density of L1 positive cells is highest in the unmyelinated proximal part of the nerve. The density of L1 mRNA positive cells in the nerve is slightly increased after a lesion (compare C and D). In the optic nerve, the distribution of cells expressing L1 (C and D) is similar to that of cells expressing GFAP (E). Scale bar in E: 100 µm (for A to E).
Figure 3B:
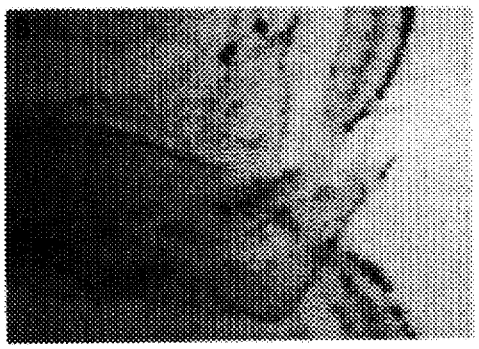
Figure 3C:
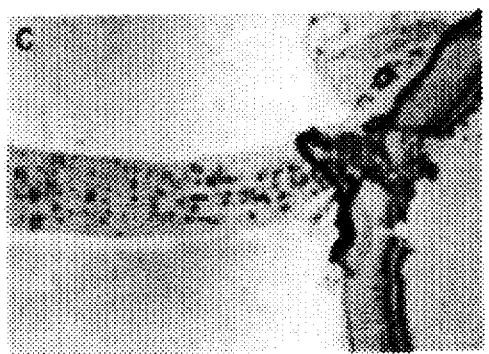

In non-transgenic controls L1 transcripts were detected only in nerve cells of the retina but not in optic nerve, neither before (FIG. 3A) nor after a lesion (FIG. 3B). By contrast, L1 mRNA was expressed by glial cells of the optic nerves from transgenic mice (FIG. 3C). L1 mRNA positive cells were detectable in both the distal myelinated and the proximal unmyelinated parts of the nerve. The intensity of the hybridization signal was higher in the unmyelinated proximal part, when compared to the myelinated distal part of the nerve.

A similar distribution of positive cells and similar differences in labelling intensity between unmyelinated and myelinated regions were observed using a GFAP cRNA probe (compare FIGS. 3C and B). The number of L1 mRNA positive cells in the optic nerve of transgenic animals was, however, always significantly lower than the number of GFAP-positive cells, probably due to the lower sensitivity of the L1 cRNA probe. Alternatively, detectable levels of L1 mRNA might be achieved only in astrocytes with high levels of GFAP expression. Such a threshold effect could be due to the design of the GFAP-L1 transgene which contains only 2 kb of GFAP 5' flanking sequences. In vitro studies suggest that the region between 2 and 6 kb upstream of the transcriptional start site contains sequence elements augmenting expression of GFAP-driven fusion genes in C6 cells (Sarid (1991) *J Neurosci.* 28:217–228). Finally, the modification of the GFAP exon 1, including the introduction of the large L1 cDNA, might reduce the stability of the chimeric mRNA as compared to GFAP mRNA and alter effects exerted by regulatory GFAP sequences located upstream and downstream of the modified region.

Figure 3D:
Figure 3E:
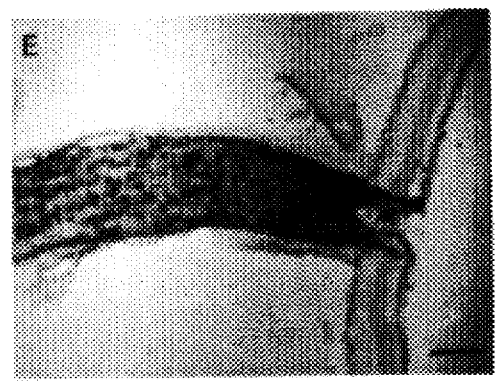

After lesioning the optic nerve, an upregulation of L1 expression was observed in transgenic (FIG. 3D) but not in nontransgenic (FIG. 3B) optic nerves. The number of cells which expressed L1 and the intensity of the L1 hybridization signal were similar in different individuals of the same transgenic line but varied across different transgenic lines. Consistent with the results obtained by Northern blot analysis (see above), L1 mRNA positive cells were most abundant in line 3426 followed by line 3427 and, finally, line 3418. This variability in the level of transgene expression in different lines could be related to a number of factors, in particular, effects caused by the neighboring host chromatin regions flanking the different transgene integration sites (Proudfoot (1986) *Nature* 322:562–565; Reik et al. (1987) *Nature* 328:248–251; Sapienze et al. (1987) *Nature* 328:251–254).

EXAMPLE 6
Antibodies

Production of polyclonal rabbit antibodies against mouse L1 and purification on an L1 immunoaffinity column (Rathjen et al. (1984); Martini et al. (1988) and polyclonal antibodies against mouse liver membrane (Lindner et al. (1983); Pollerberg et al. (1985) have been described. A mouse monoclonal antibody against GFAP was purchased (Boehringer Mannheim).

For Western blot analysis, polyclonal and monoclonal antibodies were visualized by horseradish peroxidase conjugated goat anti-mouse or rabbit antibodies (Dianova, Hamburg, Germany). For immunocytochemistry, primary antibodies were detected using fluorescein isothiocyanate- or tetramethylrhodamine isothiocyanate-conjugated goat anti-rabbit and goat anti-mouse antibodies (Dianova). Digoxigenin-labelled cRNA probes for in situ hybridization were visualized by alkaline phosphatase-conjugated Fab fragments to digoxigenin (Boehringer Mannheim).

EXAMPLE 7
Maintenance of neurons on cryostat sections

To analyze whether optic nerves from transgenic animals are more conducive to neurite outgrowth than optic nerves from wild type animals, cerebellar neurons were maintained on cryostat sections of lesioned and contralateral unlesioned optic nerves (FIG. 7).

Optic nerves of 6 to 16-week-old mice were prepared as described by Bartsch et al. (1989) *J. Comp. Neurol.* 284:451–462. In brief, lesioned and unlesioned optic nerves were embedded and frozen in serum-free, hormonally defined medium (Fischer (1986b) *Neurosci. Lett.* 28:325–329) using liquid nitrogen. Tissue sections (14 μm thick) were cut longitudinally on a Frigocut 270-cryostat (Jung-Reichardt), mounted onto poly-L-lysine-coated (Sigma, 0.001% in water) sterile glass coverslips and air-dried for 2–3 hours in a sterile chamber. After washing the sections for 5 minutes with medium, Percoll gradient-purified small cerebellar neurons (Keilhauer et al. (1985) *Nature* 316:728–730) from six-day-old ICR mice (6×10$^4$ cells in 100 μl medium) were applied to each coverslip. Cells were maintained in an incubator at 37° C. with a humidified atmosphere of 5% $CO_2$ and 95% air.

Neurite outgrowth was also measured in the presence of antibodies. Sections were pre-incubated with polyclonal L1 antibodies or polyclonal antibodies against mouse liver membranes (100 μg/ml, dialyzed extensively against and diluted in culture medium) for 1 hour at 37° C. After removal of antibodies, sections were washed carefully with culture medium (5 times, each for 5 minutes at room temperature) and Percoll gradient purified small cerebellar neurons were added. After 2 days, cryostat cultures were fixed in 4% paraformaldehyde in PBS for 30 minutes at room temperature and the neurite lengths were measured. To avoid "edge effects" in the measurements, we did not evaluate the sections which were situated in the outer rim comprising 20% of the coverslips. Using a semi-automatic computer image analysis program (IBAS, Kontron, Zeiss) the lengths of all neurites which had grown on these sections were measured and the average neurite length per neuronal cell body calculated. For each experiment and optic nerve (Lesioned or unlesioned), the average length of neurites grown on nerves of transgenic animals was related to the corresponding values of control animals. Twelve independent experiments were performed with lesioned and contralateral unlesioned nerves using at least two transgenic animals.

For transgenic animals, an increase in neurite length was observed on lesioned compared with unlesioned nerves. In contrast, neurite lengths on lesioned and unlesioned optic nerves of wild type animals were not significantly different (FIG. 8). Neurites of neurons cultured on unlesioned optic nerves from transgenic animals were consistently longer than neurites of neurons cultured on unlesioned nerves from wild type animals. A maximal increase in neurite length of about 300% was observed when using sections from line 3426. Similarly, neurite length on lesioned nerves of transgenic lines was increased up to 400% when compared with lesioned nerves from wild type animals.

The neurite outgrowth promoting activity of transgenic optic nerves correlated positively with the level of L1 expression (FIG. 8). Unlesioned optic nerves of line 3426, which express the highest levels of L1 protein were more potent in increasing neurite outgrowth than those of lines 3427 and 3418 expressing, by comparison, lower levels of L1 (in decreasing order). On lesioned optic nerves of lines 3426 and 3427 (28 days after the lesion), neurite outgrowth was four times higher than on lesioned optic nerves of wild type animals. The finding that the increase in neurite outgrowth in lesioned optic nerves was similar for the lines 3426 and 3427 (although line 3426 shows 25% increase in L1 protein expression after lesion as compared with line 3427) could indicate that the level of L1 protein in line 3427 already suffices for maximal induction of neurite outgrowth from small cerebellar neurons.

Pre-incubation of unlesioned optic nerves from wild type animals with polyclonal antibodies to L1 or mouse liver membranes did not significantly affect neurite lengths (FIG. 9). In contrast, neurite lengths were reduced by more than 50% when cryostat sections of unlesioned or lesioned optic nerves from the transgenic line 3426 were pre-incubated with L1 antibodies (FIG. 9). Antibodies to liver membranes, which strongly bind to optic nerves and small cerebellar neurons (data not shown), did not show similar inhibitory effects. Interestingly, pre-incubation of lesioned optic nerves from wild type animals with L1 antibodies induced an increase in neurite outgrowth compared with lesioned nerves from wild type animals without a prior antibody pre-incubation. Antibodies to mouse liver membranes did not show a significant increase under the same conditions, indicating that addition of cell surface reactive antibodies per se does not disturb neurite outgrowth.

EXAMPLE 8
Maintenance of neurons on monolayer cultures of astrocytes

To prepare astrocyte monolayers, forebrains from six-day-old mice were cleaned free of non-neuronal tissue and dissociated as described elsewhere (Schnitzer et al. (1981) *J. Neuroimmunol.* 1:429–456; Fischer et al. (1982a) *Neurosci. Lett.* 29:297–302; Keilhauer et al. (1985). Cells were maintained on poly-L-lysine-coated (Sigma, 0.001% in water) cell culture flasks in BME medium (Gibco) containing 10% horse serum and 2 mM glutamine for 14 to 21 days. Contaminating oligodendrocytes and neurons were removed by shaking the flasks at every medium change and by subculturing the cells at intervals of four days. Immunostaining for GFAP after 14 days of maintenance showed that more than 90% of the cells were astrocytes. After 14 days in culture, the cell were trypsinized and maintained as monolayers for five days on poly-L-lysine-coated glass coverslips. Percoll gradient purified small cerebellar neurons (Schnitzer et al. (1981)) from six-day-old mice and dorsal root ganglion (DRG) (Seilheimer et al. (1988) *J. Cell. Biol.* 107:341-351) neurons from eight-day-old chick embryos were then added onto the astrocyte monolayers. After 6 hours of co-culture for cerebellar and 12 hours for DRG neurons, the co-cultures were fixed with 2% paraformaldehyde in PBS and neurite lengths were analyzed as described in Example 7.

Figure 10A:
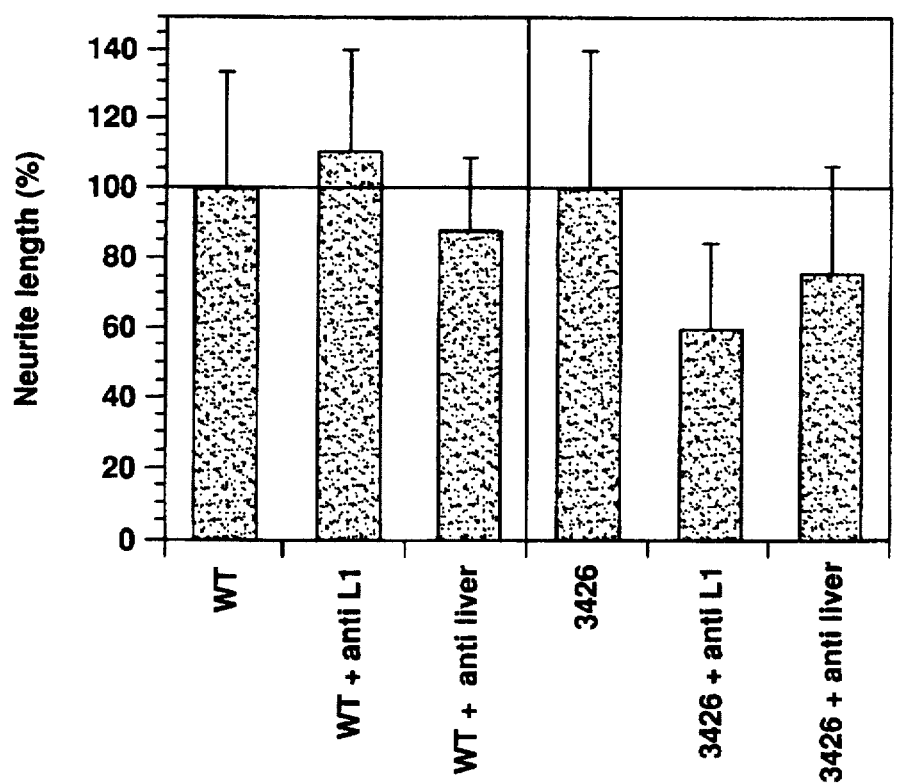
FIG. 10 depicts and compares neurite lengths of mouse cerebellar (A) or chick DRG (B) neurons on astrocytic monolayers prepared from wild type (WT) and transgenic animals (line 3426) in the absence of antibodies and after pre-incubation of sections with affinity purified polyclonal antibodies against L2 (anti L1) and mouse liver membranes (anti liver). The neurite length on astrocytes without pre-incubation with any antibody was taken as 100% and the neurite lengths on astrocyte monolayers obtained after antibody treatment are expressed in relation to this value. A significant reduction (about 40%) of neurite length is only visible on transgenic astrocytes after preincubation of the monolayers with L1 antibodies. Mean values ± standard deviation are from at least 100 neurons from two independent experiments carried out in quadruplicate. * indicates means that were significantly different ($p<0.05$, Mann-Whitney U test) from the control (wild type or transgenic astrocytes without any antibody treatment).
Figure 10B:
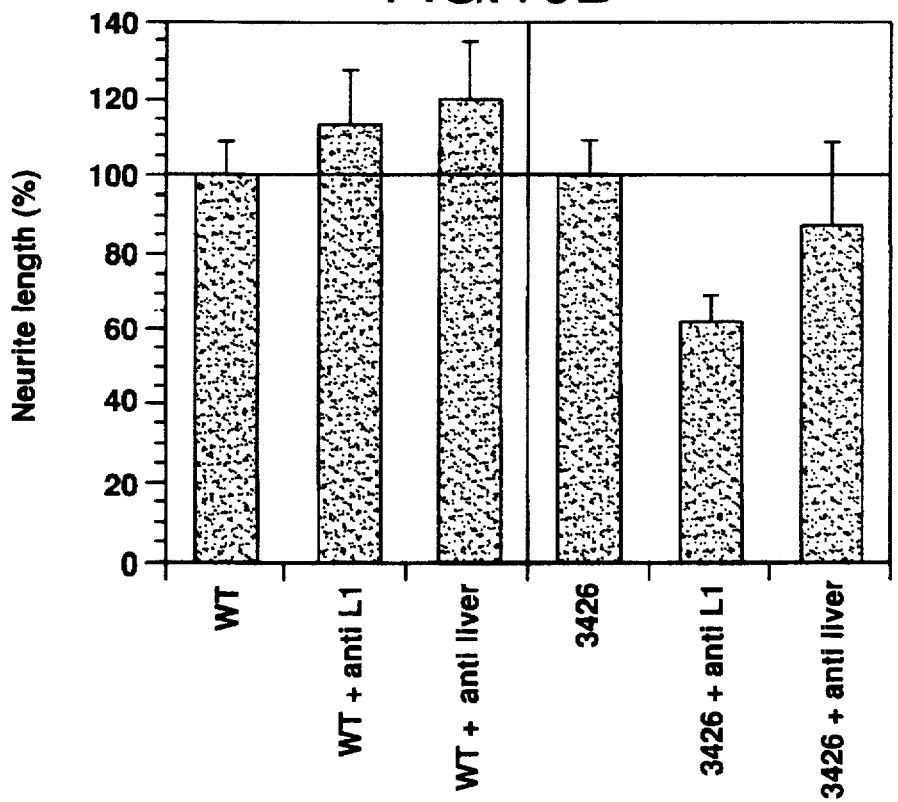

Neurite outgrowth from mouse small cerebellar or chick dorsal root ganglion (DRG) neurons was also studied in monolayer cultures of astrocytes derived from transgenic (line 3426) or non-transgenic controls (FIG. 10, Table 1).

TABLE 1

Neurite lengths of cerebellar and dorsal root ganglion (DRG) neurons maintained on astrocytic monolayers prepared from wild type mice (WT) and the transgenic line 3426.

|               | Cerebellar neurons | DRG neurons    |
|---------------|--------------------|----------------|
| WT            | 65 × 34 mm         | 90 × 10 mm     |
| WT + anti L1  | 72 × 30 mm         | 105 × 14 mm    |
| WT + anti liver | 57 × 24 mm       | 107 × 12 mm    |
| 3426          | 75 × 41 mm         | 137 × 10 mm    |
| 3426 + anti L1 | 45 × 25 mm        | 88 × 5 mm      |
| 3426 + anti liver | 58 × 31 mm     | 124 × 15 mm    |

Neurite lengths on astrocytes without pre-incubation with any antibody or after treatment with polyclonal antibodies against L1 (anti L1) or antibodies against mouse liver membranes (anti liver) are shown. Mean values ± standard deviation are from at least 100 neurons from two independent experiments carried out in quadruplicate.

Neurite length of cerebellar or DRG neurons on transgenic astrocytes was approximately 15% or 50% higher, respectively, when compared with neurite length using wild type astrocytes (Table 1). Anti-liver membrane antibodies did not affect neurite length on astrocyte monolayers from wild type or transgenic animals (FIG. 10, Table 1). Pre-incubation of astrocyte monolayers with L1 antibodies did not significantly affect neurite length on cells from wild type animals. In contrast, it reduced neurite length of cerebellar or DRG neurons grown on cells from transgenic animals by approximately 40%. It is noteworthy in this context that the polyclonal antibodies directed against mouse L1 used in this study do not react with neurons from chicken (Martini et al., 1994a; data not shown). By immunofluorescence analysis it could be shown, however, that these antibodies bind as efficiently as L1 antibodies to astrocytes from transgenic animals as well as to mouse small cerebellar neurons (data not shown).

EXAMPLE 9
Immunofluorescence and Aurion-GP immunogold microscopy

L1 and GFAP immunostaining of fresh-frozen cross- or longitudinally sectioned optic nerves or astrocytic monolayers of wild type and transgenic animals were performed as described (Bartsch et al. (1989)). For double-labelling, we first incubated astrocytes as live cells with L1 antibodies (2 µg/ml in 1% BSA in PBS) at 4° C. for 30 minutes. After permeabilizing the cells with 70% methanol at −20° C. for 10 minutes, cells were incubated with GFAP antibody for 30 minutes at 4° C.

For quantification of neurite lengths in cryostat culture experiments, the Aurion immuno R-Gent silver enhanced staining was used according to the manufacturer's instructions (Aurion, Immuno Gold Reagents & Accessories Custom Labelling, Wageningen, The Netherlands) with minor modifications. In brief, cultures were fixed in 4% paraformaldehyde in PBS for 10 minutes at room temperature, incubated in 50 mM glycine in PBS for 10 minutes and then treated for 15 minutes in blocking buffer (BB, 0.5% BSA in PBS). After 3 washes in BB, each for 5 minutes, cells were incubated with L1 antibodies diluted in BB (2 µg/ml) for 30 minutes at room temperature. Subsequently, cultures were washed 3 times in BB each for 5 minutes and secondary antibody diluted 1:20 in BB was added for 1 hour at room temperature. After 3 washes with distilled water, cultures were fixed in 2% glutaraldehyde in PBS for 10 minutes at room temperature and washed 3 times with distilled water. A 1:1 mixture of enhancer and developer was then added at room temperature. After the appearance of the reaction product, coverslips were washed 3 times with distilled water and embedded in glycerol.

Figure 4A:
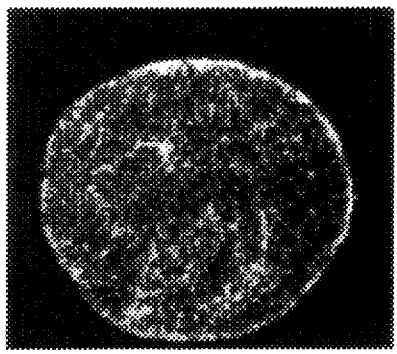
FIG. 4 depicts the double immunofluorescence microscopic localization of L1 (A and B) and GFAP (C) in unlesioned (A and C) and lesioned (28 days after the lesion, B) optic nerves from adult transgenic (line 3426, A and B) and wild type (C) animals. L1 immunoreactivity in optic nerves from transgenic animals is significantly increased after a lesion (compare A and B). The pattern of L1 immunoreactivity in lesioned transgenic nerves is similar to the pattern of GFAP immunostaining in unlesioned wild type nerves. L1 positive unmyelinated retinal cell ganglion axons are present in unlesioned wild type nerve (A). Scale bar in C:50 µm (For A to C).
Figure 4B:
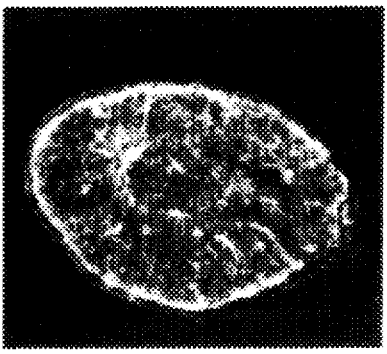
Figure 4C:
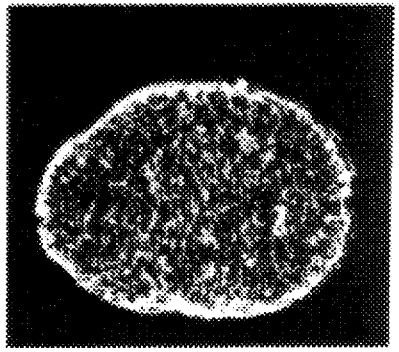

In optic nerves of non-transgenic mice, L1 immunoreactivity was restricted to unmyelinated retinal ganglion cell axons (Bartsch et al. (1989)). In unlesioned optic nerves from transgenic animals, weak L1 immunoreactivity was also found in association with cell bodies and radially oriented cell processes (FIG. 4A). The intensity of this L1 immunoreactivity in transgenic optic nerves increased significantly after a lesion (FIG. 4B) and was similar in distribution to the GFAP immunoreactivity found in unlesioned (FIG. 4C) or lesioned (not shown) wild type nerves.

L1 expression was additionally analyzed in cultures of astrocytes prepared from forebrain of six-day-old transgenic animals. No L1 immunoreactivity was detectable on astrocytes from wild type animals (FIG. 5D). In contrast, L1 positive cells were present in cultures from transgenic animals (FIG. 5A). As demonstrated by double-immunostaining, the same cells also proved positive for GFAP (FIG. 5B and E) indicating that the cells expressing L1 are indeed astrocytes. Since L1 immunostaining was performed on living cells, it seems likely that in the transgenic animals L1 is also exposed on the cell surface of astrocytes in vivo.

EXAMPLE 10
Western blot analysis

Figure 6:
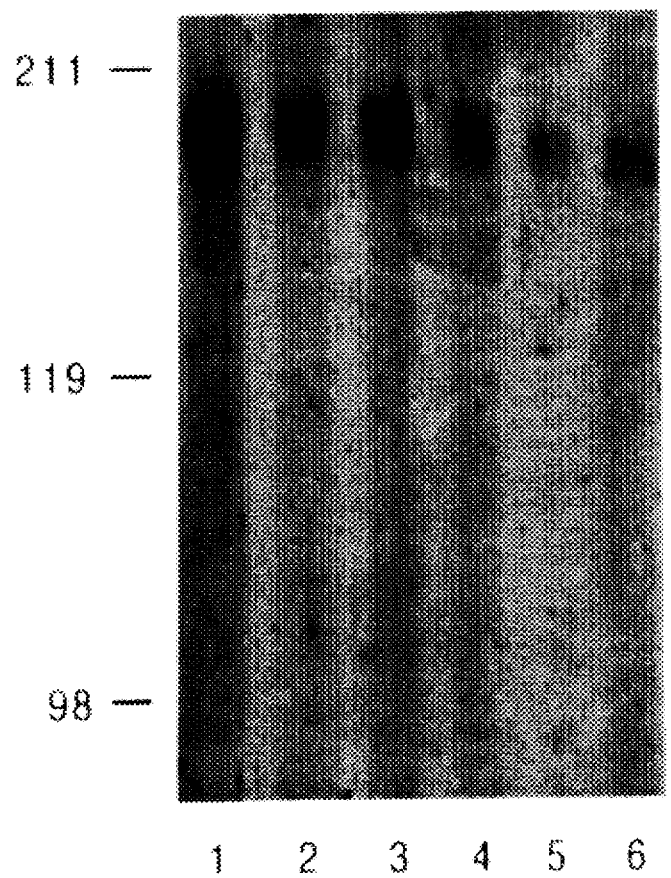
FIG. 6 shows (A) Western blot analysis of lesioned (15 days after the lesion) and unlesioned optic nerves from transgenic and wild type animals. 25 μg of total protein of lesioned (lanes 1, 3 and 5) or unlesioned nerves (lanes 2, 4, and 6) was loaded and detected using affinity purified polyclonal antibodies against L1. Protein extracts were made from mice of transgenic lines 3426 (lanes 1 and 2), 3427 (lanes 3 and 4) and from wild type animals (lanes 5 and 6). There is an increase in L1 expression in transgenic animals compared to non-transgenic controls. Following optic nerve lesion, an up-regulation of L1 occurred in transgenic animals, whereas the amount of L1 in wild type animals decreased. Apparent molecular weights (in kD) are shown on the left margin.

To further quantitate the amount of L1 expression in GFAP-L1 transgenic mice, detergent extracts of homogenates of unlesioned and lesioned (15 days after the lesion) optic nerves from wild type and transgenic adult mice were analyzed on Western blots (FIG. 6).

Lesioned (15 days after the lesion) and contralateral unlesioned optic nerves from 8-week-old animals were cleaned free of non-neuronal tissues and then frozen in liquid nitrogen. Care was taken that only myelinated distal but not L1 immunoreactive unmyelinated or partly myelinated proximal regions of the nerves were used. Nerves were frozen and thawed ten times before sonication with a Branson B15 sonicator at 4° C. for 5 minutes. The tissues were then homogenized with a Dounce homogenizer in homogenization buffer (1% Triton X-100, 2M urea, 5 mM benzamidine, 0.1 mM iodoacetamide, 1 mM phenylmethanesulfonyl fluoride, 5 mM Na-p-tosyl-L-lysinechloromethyl ketone in PBS). Homogenates were cleared by centrifugation at 16,000 g at 4° C. for 15 minutes. Supernatants were treated with methanol/chloroform to precipitate proteins as described by Wessel et al. (1984). The protein content was determined in the supernatant (Pierce). After SDS-PAGE on 7% slab gels under reducing conditions, proteins (25 µg) were analyzed by Western blotting using polyclonal L1 antibodies (0.4 µg/ml). Horseradish peroxidase-conjugated secondary antibody (2 µg/ml) was detected by the ECL Western blotting detection kit (Amersham). Densitometric analysis of immunoblots was performed on scanned images (Arcus scanner, Agfa- Gavaert) of the original films using the Image Program (NIH, Research Services Branch, NIMH).

Densitometric analysis of the immunoblots demonstrated that L1 expression in unlesioned optic nerves of transgenic animals was about 40% and 13% (lines 3426 and 3427, respectively) higher than in unlesioned optic nerves of wild type animals. L1 expression in lesioned transgenic nerves was 310% and 200% (lines 3426 and 3427, respectively) higher as compared with lesioned nerves of wild type animals. A comparison between lesioned and contralateral unlesioned optic nerves from wild type animals revealed a decrease in L1 protein expression of about 40% on the lesioned side. In contrast, the amount of L1 protein in lesioned nerves of lines 3427 and 3426 increased by approximately 30% when compared with the unlesioned contralateral side. The expression level of L1 in line 3426 was approximately 35% and 25% higher than in the line 3427 for unlesioned and lesioned optic nerves, respectively.

EXAMPLE 11
In vivo regrowth of axons in the optic nerve

Figure 11:
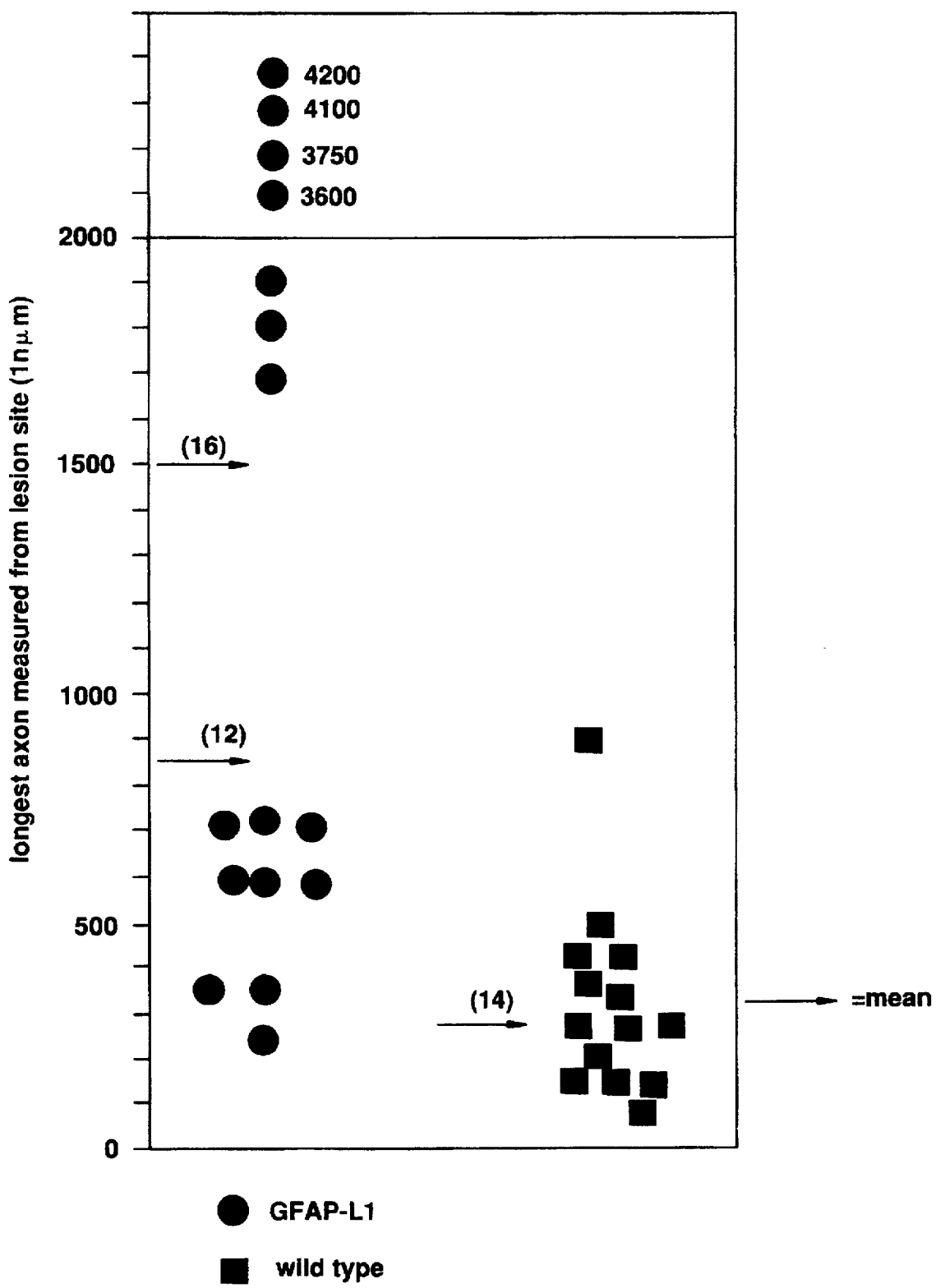
FIG. 11 demonstrates the in vivo regrowth of axons in the optic nerve (0–2000 μm). 6–8 week old GFAP-L1 transgenic mice and wild type mice were crushed intraorbitally and, after 14 days, traced with a fluorescein-labeled biotin ester to mark retinal ganglion cell axons by anterograde labeling. Each point represents one animal.
Figure 12:
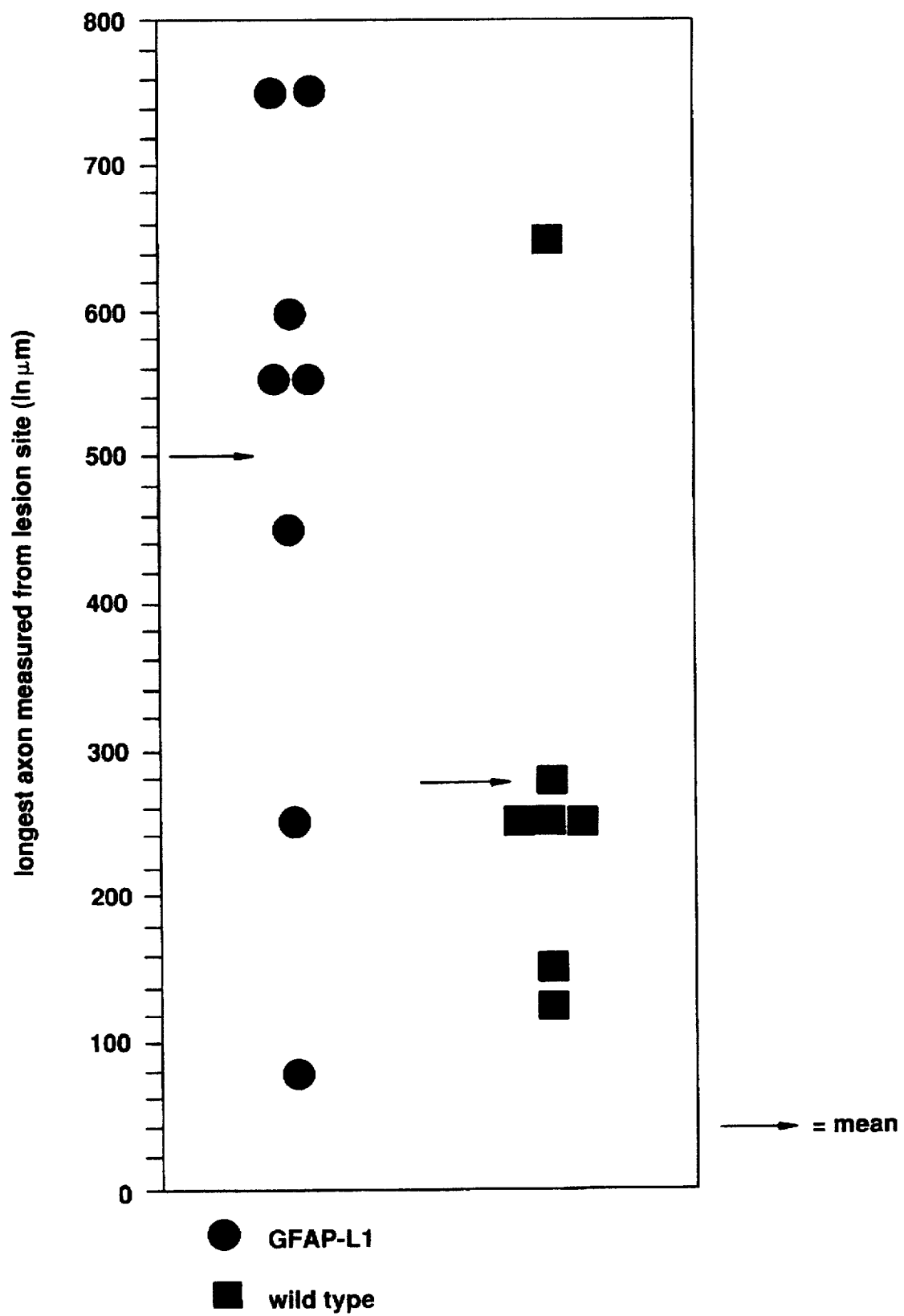
FIG. 12 depicts in vivo regrowth of axons in the optic nerve (0–800 μm). 6–8 week old GFAP-L1 transgenic mice and wild type mice were crushed intraorbitally and, after 14 days, traced with a fluorescein-labeled biotin ester to mark retinal ganglion cell axons by anterograde labeling. Each point represents one animal.

6–8 week old GFAP-L1 transgenic mice and wild type mice were crushed intraorbitally and, after 14 days, traced with a fluorescein-labeled biotin ester to ark retinal ganglion cell axons by anterograde labeling. Results are shown in FIGS. 11 and 12. Each point represents one animal.

EXAMPLE 12
Identification of the border between fibronectin type III homologous repeats 2 and 3 of the neural cell adhesion molecule L1 as a neurite outgrowth promoting and signal transducing domain To determine the domains of neural cell adhesion molecule L1 involved in neurite outgrowth, monoclonal antibodies against L1 were generated and their effects on neurite outgrowth of small cerebellar neurons in culture investigated. When the eleven antibodies were coated as substrate, only antibody 557.B6, which recognizes an epitope represented by a synthetic peptide comprising amino acids 818 to 832 at the border between the fibronectin type III homologous repeats 2 and 3, was as potent as L1 in promoting neurite outgrowth, increasing intracellular levels of $Ca^{2+}$ and stimulating the turnover of inositol phosphates. These findings suggest that neurite outgrowth and changes in these second messengers are correlated. Such a correlation was confirmed by the ability of $Ca^{2+}$-channel antagonists and pertussis toxin to inhibit neurite outgrowth on L1 and antibody 557.B6. These observations indicate for the first time a distinct site on cell surface-bound L1 as a prominent signal transducing domain through which the recognition events appear to be funnelled to trigger neurite outgrowth, increase turnover of inositol phosphates and elevate intracellular levels of $Ca^{2+}$.

EXAMPLE 13
L2/HNK-1 immunoreactivity in reinnervated peripheral nerve: preferential expression of previously motor axon-associated Schwann cells The carbohydrate epitope L2/HNK-1 (hereafter designated L2) is expressed in the adult mouse by myelinating Schwann cells of ventral roots and muscle nerves, but rarely by those of dorsal roots or cutaneous nerves. Since substrate-coated L2 glycolipids promote outgrowth of cultured motor but not sensory neurons, L2 may thus influence the preferential reinnervation of muscle nerves by regenerating motor axons in vivo.

Therefore, the influence of regenerating axons on L2 expression by reinnervated Schwann cells was analyzed by directing motor or sensory axons into the muscle and cutaneous branches of femoral nerves of eight-week-old mice. Regenerating axons from cutaneous branches did not lead to immunocytochemically detectable L2 expression in muscle or cutaneous nerve branches. Axons regenerating from muscle branches led to a weak L2 expression by few Schwann cells of the cutaneous branch, but provoked a strong L2 expression by many Schwann cells of the muscle branch. Myelinating Schwann cells previously associated with motor axons thus differed from previously sensory axon-associated myelinating Schwann cells in their ability to express L2 when contacted by motor axons. This upregulation of L2 expression during critical stages of reinnervation may provide motor axons regenerating into the appropriate, muscle pathways with an advantage over those regenerating into the inappropriate, sensory pathways.

EXAMPLE 14
L1 in consolidation of memory for a passive avoidance task in the chick Training day-old chicks on a one trial passive avoidance task, in which they learn to suppress their tendency to peck at a small bright bead if it is coated in the bitter-tasting methylanthranilate, results in a time-dependant cellular and molecular cascade culminating in the remodelling of pre- and post-synaptic elements in two discrete regions of the forebrain, the intermediate medial hyperstriatum ventrale (IMHV) and Lobus parolfactorius (LOP) (Rose (1991) *Trends In Neurosciences* 14:390–397). The cascade involves two distinct waves of glycoprotein synthesis, as evidenced by enhanced fucose incorporation, occurring in both IMHV and LPO at varying times following training. Both waves are necessary for long-term (that is, 24 hours plus) memory retention for the avoidance tasks, in which amnesia is evidenced by chicks, which would otherwise avoid the previously bitter bead, pecking at a dry bead on test.

Given the role of L1 in mediating cell-cell contact, the present study was undertaken in order to determine if L1 is amongst the learning-associated glycoproteins participating in either or both waves of glycoprotein synthesis, and is necessary for memory formation. If so, antibodies to L1 administered at an appropriate time relative to training should prevent the synaptic remodelling necessary for long term memory and therefore produce amnesia for the task. Similarly, if the extracellular domains of the L1 molecule play a part in the recognition and adhesion processes which are required for synaptic remodelling and stabilization, exogenously applied extracellular domain fragments which will bind homophilically to the endogenous molecule might disrupt this process.

Antibodies and Fragments

Polyclonal antibodies were prepared in rabbits by immunization with immunoaffinity purified L1 (Ng-CAM, 8D9) following an established immunization procedure (Rathjen et al. (1984)). L1 was isolated from one-day old chicken brains using an 8D9 monoclonal antibody (Lagenaur and Lemmon (1987) *Proc. Nat'l Acad. Sci. USA* 84:77533–7757) column again using established procedures (Rathjen et al. (1984)). Antibodies were isolated from the serum obtained after the third immunization using Protein G Sepharose (Pharmacia LKB) according to the manufacturer's instructions. Recombinantly expressed fusion proteins in *E. coli* representing the six immunoglobulin-like (Ig-I–VI) and five fibronectin type III homologous repeats (FN1–5) were prepared as described by Appel et al (1993). Sodium dodecyl sulfate polyacrylamide gel electrophoresis (SDS-PAGE) and immunoblots of chick subcellular fractions Fifty μg of protein from brain homogenate, from crude membranes, from a soluble fraction (Burchuladze et al. (1990) *Brain Res.* 535:131–138) and from postsynaptic densities (Murakami et al. (1986) *J. Neurochem.* 46:340–348), all from day-old chicken brains were separated by SDS-PAGE under reducing conditions on a 5–15% polyacrylamide gradient gel (Laemmli (1970) *Nature* 227:146–148), whereafter they were transferred to nitrocellulose according to the method of (Burnette (1981) *Anal. Biochem.* 112:195–203). After overnight incubation with L1 antibodies at a dilution of 1:1,000 in Tris-buffered saline, pH 7.2, containing 5% defatted milk powder, immunoreactive bands were detected according to previously described methods (Scholey et al. (1993) *Neurosciences* 55:499–509).

Training and testing procedures

Day-old Ross chunky chicks of both sexes, hatched in incubators were place in pairs in small pens, pretrained to peck at small (2.5 mm) white beads and then trained on a larger (4 mm) chrome bead coated with methylanthranilate as described by Lossner and Rose ((1983) *J. Neurosciences* 41:1357:1363). Birds which pecked the bitter bead evinced a stereotyped disgust response, shaking their heads vigorously and backing away from the bead. Twenty four hours following training, each animal was tested by the presentation of a dry chrome bead identical to the one used in training. Retention of passive avoidance learning was indicated in animals avoiding the test bead. In each replication of this protocol, 24–36 chicks were trained and tested. More than 80% of trained, uninjected chicks normally avoid the bead on test under these conditions, though there is sometimes a slight reduction in avoidance in saline injected birds. By contrast, birds which are trained on a water-coated bead peck the dry bead avidly on test, and their avoidance score is rarely above 5–10%. All training and testing was routinely carried out by an experimenter blind as to the prior treatment of the animals.

Injections

Figure 13:
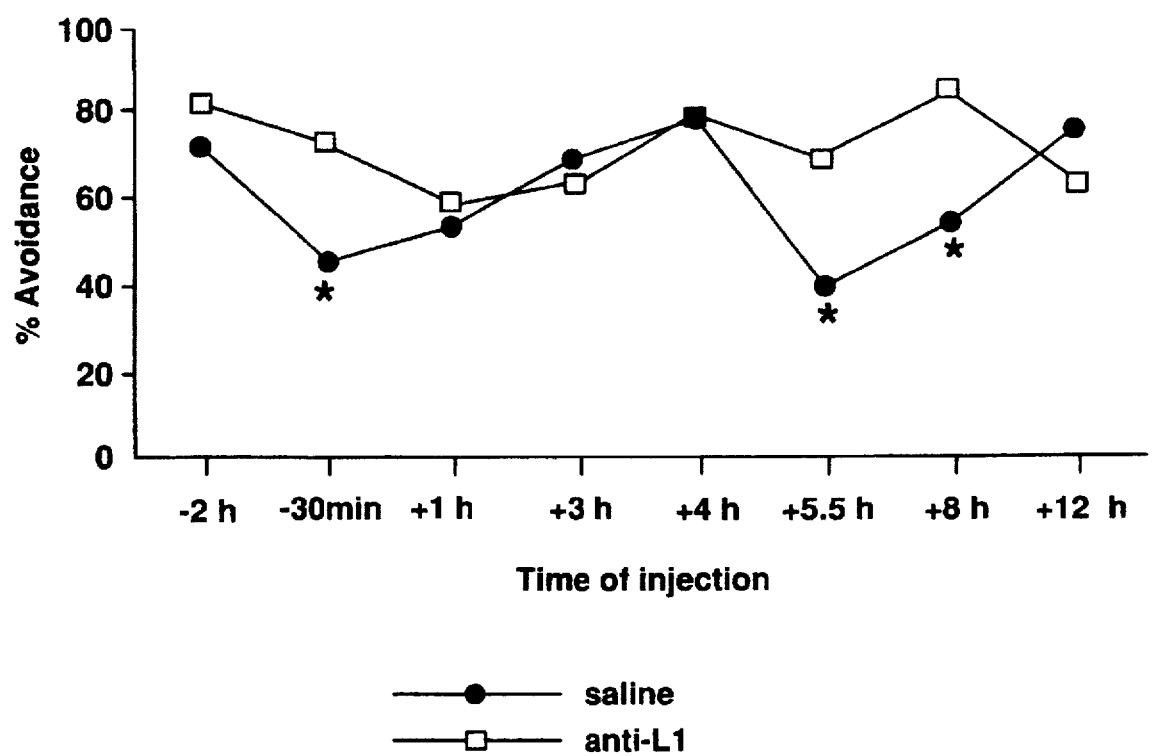
FIG. 13 shows the effect of the injection of chicken L1 antibodies into the IMHV on percent avoidance (retention of memory) on a one-trial passive avoidance task. Each point represents a group of birds who received injections of L1 antibodies (anti-L1) (closed circles) or saline (open squares) at the time relative to training indicated. All animals were tested at 24 hours post-training (*, $p<0.05$ between saline and antibody groups, $\chi^2$).
Figure 14A:
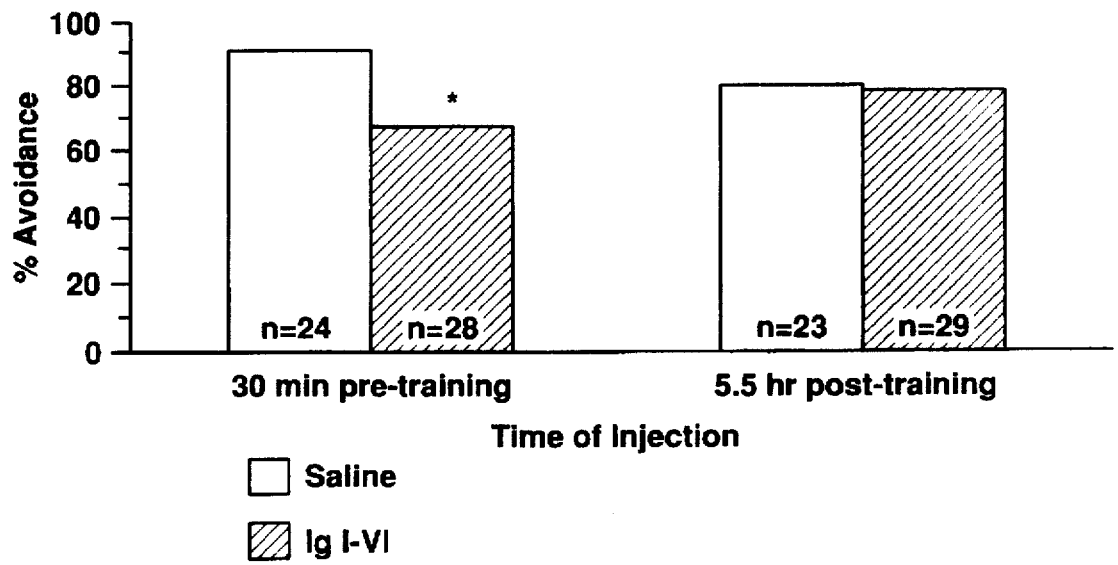
FIG. 14 comprises two graphs depicting the effect of injections of Ig I–IV and FN fragments at −30 minutes and +5.5 hours on retention of memory for passive avoidance task. All animals were tested at 24 hours post-training. The number of animals in each group is shown in the histograms (*$p<0.05$; **$p<0.005$).
Figure 14B:
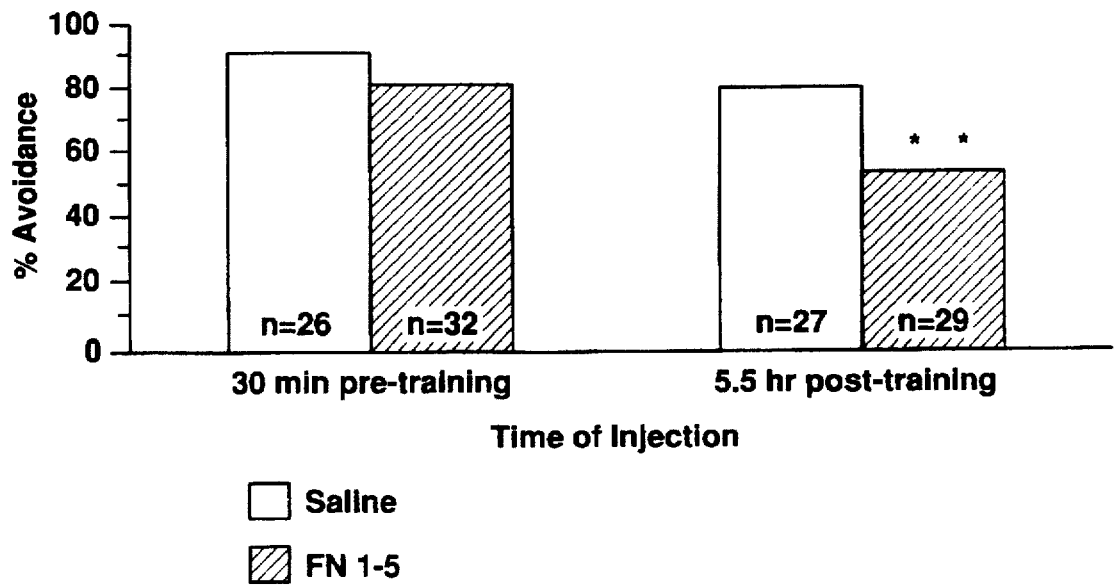
Figure 15A:
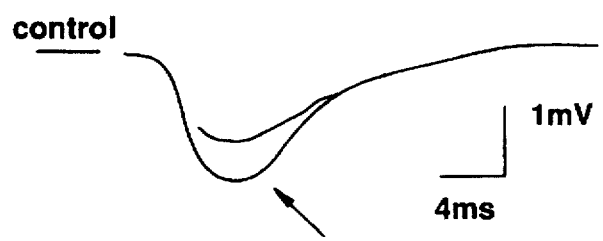
FIG. 15 comprises a series of graphs showing the influence of antibodies against L1 (anti-L1) on LTP in pyramidal neurons in the CA1 region of rat hippocampal slices. a. Averaged (n=4) EPSP's recorded before and 50 minutes after (arrow) TBS at the control site not injected with antibodies. b. Averaged (n=4) EPSPs recorded before and 50 min. after TBS (arrow) in the presence of rabbit polyclonal antibodies against mouse L1 (Rathjen et al. (1984)). c. Time-course of the EPSP initial slope before and after TBS in the presence of L1 antibodies (IgG fraction, 6.2 mg/ml ○) or polyclonal antibodies to the immunoglobulin-like domains I–VI recombinantly expressed in CHO cells (Hynes (1992) Cell. 69:11–25) (antiserum containing approximately 1 mg/ml of specific antibodies, ▼) and the following controls: (1) Control LTP (no antibodies, □), (2) in the presence of the IgG fraction of the polyclonal antibodies to mouse liver membranes (3.5 mg/ml, ●), which react strongly with rat hippocampal slices (Lindner et al. (1983) Nature 305:427–430), (3) in the presence of rabbit non-immune serum, and (4) in the presence of L1 antibodies without induction of LTP by TBS (6.2 mg/ml, ○; see also e, f). Results are expressed as means ± S.E.M. of the EPSP initial slope i percent of the baseline values recorded during the 20 min. before TBS (n=5) slices from at least 3 animals; values for LTP's in the presence of L1 antibodies differ from the control LTP at $p<0.001$ for the antibodies against L1, and at $p<0.01$ for the antibodies to the immunoglobulin-like domains I–VI). d. Concentration-dependence of the reduction in LTP by the IgG fraction of polyclonal antibodies against L1 (6.2 mg/ml; ○); 2 mg/ml, ●; 0.6 mg/ml, ▲; 0.06 mg/ml, □; $p<0.0001$). As a control, the results from polyclonal antibodies against liver membranes are shown (3.5 mg/ml, ■). e. Averaged (n=4) EPSP's recorded before and 60 min. after (arrow) the application of polyclonal antibodies against L1 in the absence of TBS. f. Averaged (n=4) intracellular excitatory postsynaptic currents (EPSP) recorded before and 30 min. after (arrow) the application of polyclonal antibodies against L1 in the absence of TBS.
Figure 15B:
Figure 15C:
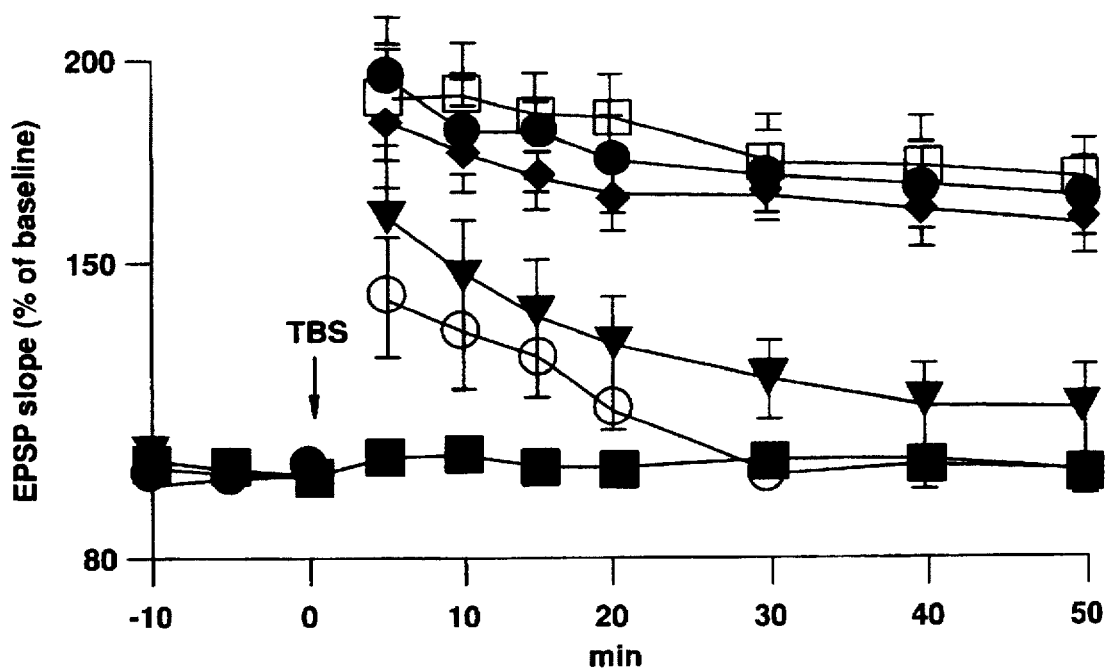
Figure 15D:
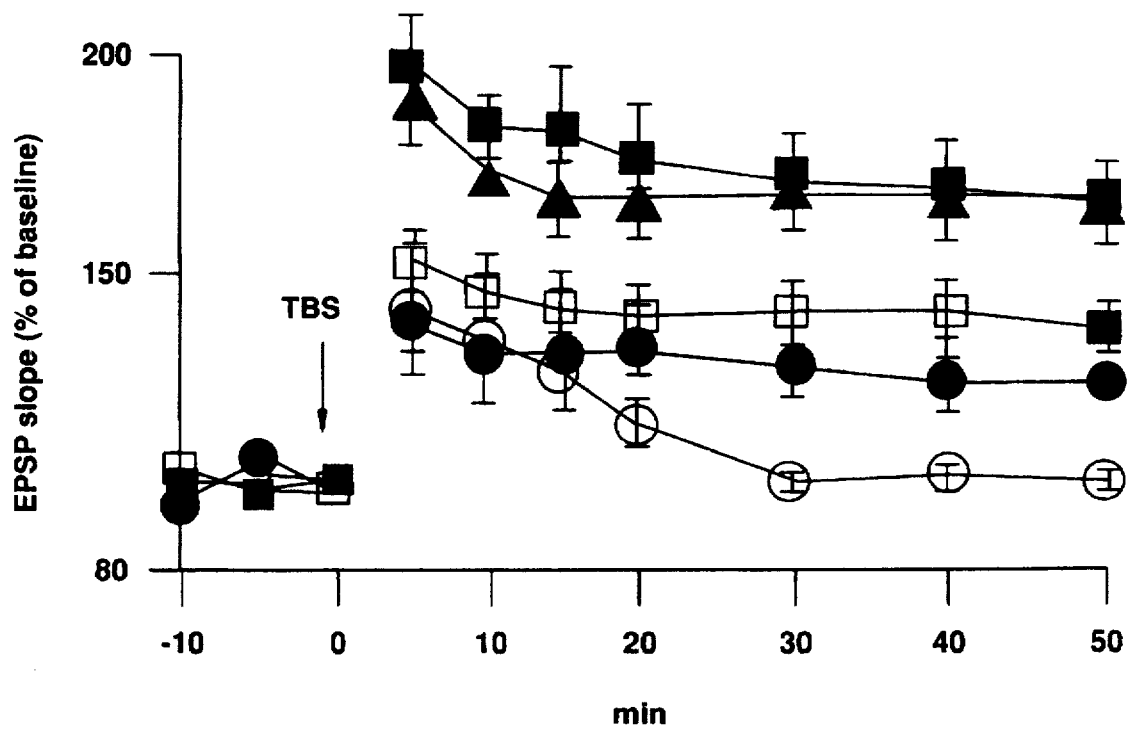
Figure 15E:
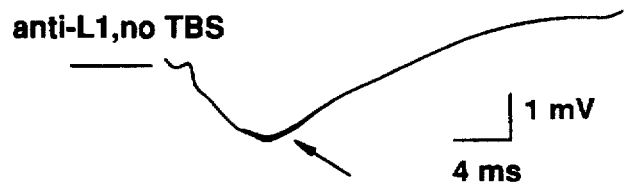
Figure 15F:
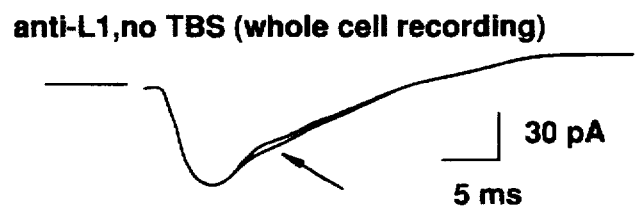

L1 antibodies, FN1–5 and Ig I–VI fragments were dialyzed overnight against 0.9% saline and the concentration adjusted to 1 mg/ml for L1 and 250 μg/ml for the fragments. Chicks received bilateral intracranial injections into the intermediate medial hyperstriatum ventrale (IMHV) of 10 l L1 antibodies per hemisphere; control animals received similar injections of saline. Accurate delivery into the IMHV was received by the use of a specially designed head holder and sleeved Hamilton syringe (Davis et al. (1982) *Pharm. Biochem. Behav.* 17:893–896). Chicks receiving this injection volume of either saline or antibodies prior to training or testing showed no overt behavioral effects, pecking the bead accurately during training. The large extracellular volume of the brain of the newly hatched chick means that injections of this size are well-tolerated, and can be achieved without leakage. A previous report has demonstrated (Scholey et al. (1993)) that there is a slow diffusion of antibody from the injection site in the hours following injection. The accuracy of placement of the injection was routinely monitored by visual inspection of the brains post-mortem. In each replication of the experiment, a balanced group of saline and antibody or fragment-injected chicks were employed. In the L1 experiment, groups of chicks were injected with saline or antibody at one of eight time points relative to training; 2 hours or 30 minutes pretraining, or +1 hour, +3 hours, +4 hours, +5.5 hours, +8 hours or +12 hours post-training. On the basis of previous observations, it was predicted that any effects would be observed in birds injected at either 30 minutes prior or 5.5 hours post-training, and the numbers of replications at these time points were accordingly greater (N=17, 28, 17, 19, 18, 21, 19 and 18 respectively for antibody injections). L1 fragments FN1–5 and Ig I–IV were injected at either –30 minutes or +5.5 hours and retention tested at 24 hours. Retention in groups of saline and L1-antibody or L1-fragment-injected chicks was compared statistically by $\chi^2$. Results are shown in FIGS. 13 and 14.

EXAMPLE 15

Involvement of L1 and NCAM in long term potentiation

Transverse hippocampal slices (400 μm) from halothane-anaesthetized male Wistar rats (180–220 g) were prepared using standard techniques. Slices were maintained in an interface chamber and initially allowed to recover for 45 min. in a hyperosmolar (320 mOsm/kg) artificial cerebrospinal fluid (ACSF) at room temperature. The bath temperature was then raised to 30° C. and the medium was changed to a normotonic ACSF (307 mOsm/kg) containing (in mM): NaCl, 124.0; KCl, 2.5; MgSO$_{24}$, 2.0; CaCl$_2$, 2.5; KH$_2$PO$_4$, 1.25; NaHCO$_3$, 26.0; glucose, 10; sucrose, 4; bubbled with 95% O$_2$/5% C0$_2$ (pH 7.4); perfusion rate: 0.75 ml/min. The Schaffer collateral/commissural fibers were stimulated by twisted platinum-iridium wires (50 μm diameter) placed in the stratum radiatum of the CA1 region. Test stimuli consisted in monophasic impulses of 100 μs duration every 30 seconds and the stimulus strength was adjusted to obtain 30% of the maximal EPSP amplitude (maximal EPSP without superimposed population spike). EPSP's were recorded from the CA1 stratum radiatum by means of 2 glass micropipettes (2M NaCl, 1–5 MΩ) positioned about 300 μM apart from the stimulation electrode on each side.

After stable recording for at least 15 minutes, antibodies or protein fragments were ejected onto the CA1 dendritic field in the vicinity (50–75 μm) of one recording electrode (the one carefully adjusted at 30%) by using a modified microinjection system (Nanoliter injector, WPI) continuously delivering 5 nl every 10 seconds up to the end of the experiment unless otherwise indicated. A wash-out of the antibodies with subsequent induction of LTP was not possible for evident reasons, but it was verified whether LTP could be induced within each slice by recording from the second electrode where no antibodies were applied. Although the tip of the ejection micropipette did not penetrate the slice, a small reduction in the EPSP amplitude was sometimes observed when the ejection was started. This volume artifact was independent of the nature of the ejected material. Proteins were dialyzed against 20 mM PBS at pH 7.4 unless otherwise indicated and concentrations referred to the pipette concentration.

Twenty minutes after initiating the microejection, LTP was induced with a theta burst stimulation (TBS) paradigm consisting of three trains spaced by 4 seconds; each train consisted of ten high frequency bursts of 5 pulses at 100 Hz and the bursts were separated by 200 ms (Reichardt et al. (1991) *Annu. Rev Neurosci.* 14:531–570). Duration of the stimulation pulses was doubled during TBS. Induction of LTP could be totally prevented by perfusion of 10 μM D(−)-2-amino-5-phosphonopentanoic acid (D-AP5; Tocris). Whole cell recordings were obtained from CA1 neurons using the "blind" patch clamp method with an EPC-9 patch clamp amplifier. The bath temperature was 30° C. Patch electrodes were pulled from 1.5 mm OD borosilicate glass and had resistances between 3 and 8 MΩ. The pipettes were neither fire polished nor coated. The electrodes were routinely filed with a solution containing (in mM): potassium gluconate, 129; KCl, 5; MgCl$_2$, 1; CaCl$_2$, 1; N-(1-hydroxyethyl)-piperazine-N'-(2-ethanesulphonic acid) (HEPES), 5; 1,2-bis(2-aminophenoxy)ethane-N,N,N',N'-tetraacetic acid (BAPTA), 5; Na-ATP, 10 and Na-GTP, 0.3, with pH adjusted to 7.3 using KOH. Series resistance was not compensated. Responses were sampled as an average of three to four signals, either printed out for visual analysis, or stored on disk for further analysis. Statistical evaluations were performed by analysis of variances with planned comparisons and contrast analysis; time was considered as a dependent variable with one level of repeated measures. Anti-L1 (Rathjen et al. (1984)), anti-Ig I-VI (Hynes et al. (1992)) and anti-liver membranes antibodies (Linder (et al. (1983)) were produced as previously described. Results are shown in FIG. 15.

Figure 16A:
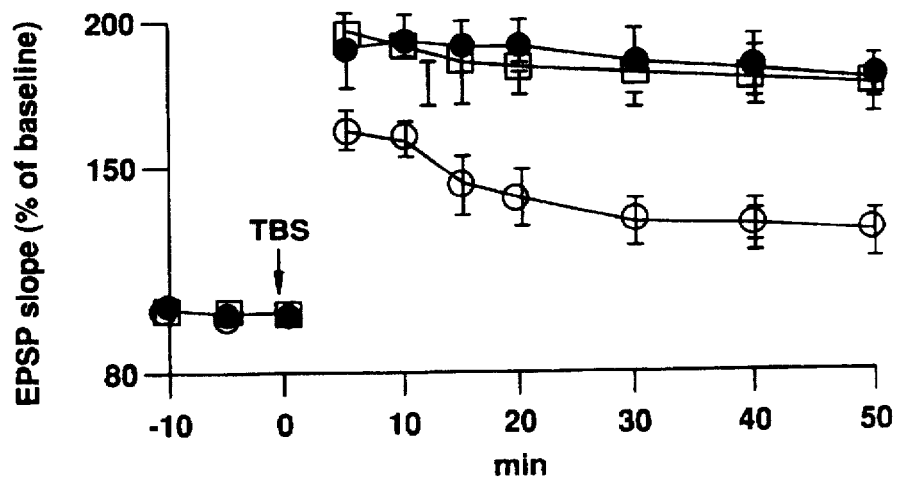
FIG. 16 demonstrates the influence of the immunoglobulin-like domains I–VI, polyclonal NCAM antibodies and oligomannosidic glycopeptides on LTP. a. time-course of the EPSP initial slope before and after TBS in the presence of the immunoglobulin (Ig)-like domains I–VI (216 µg/ml; 3.2 mM; in 20 mM Tris/HCl pH 7.6 ○; p<0.01) and the fibronectin (FN) type III homologous repeats I–V (225 µg/ml; 3.8 mM; in 20 mM Tris/HCl pH 7.6, ■) of L1, compared to control LTP (20 mM Tris/HCl, pH 7.6, □). b, Time-course of the EPSP initial slope before and after TBS in the presence of antibodies to NCAM (IgG fraction, 3.9 mg/ml,▲), an antiserum against axonin-1 (●), and the following controls: (1) a non-immune rabbit serum (▲), (2) an IgG fraction of non-immune rabbit serum (3.0 mg/ml, ♦), and (3) in the presence of NCAM antibodies (3.9 mg/ml,□; p<0.06) without induction of LTP by TBS. c, time-course of the EPSP initial slope before and after TBS in the presence of oligomannosidic glycopeptides (○), control glycopeptides (●) derived from asialofetuin (both at 100 µM), and in the absence of glycopeptides (□). Results are expressed as means ± S.E.M. of the EPSP initial slope in percent of the baseline values recorded during the 20 min. before TBS (n=5 or 6 slices from at least 3 animals).
Figure 16B:
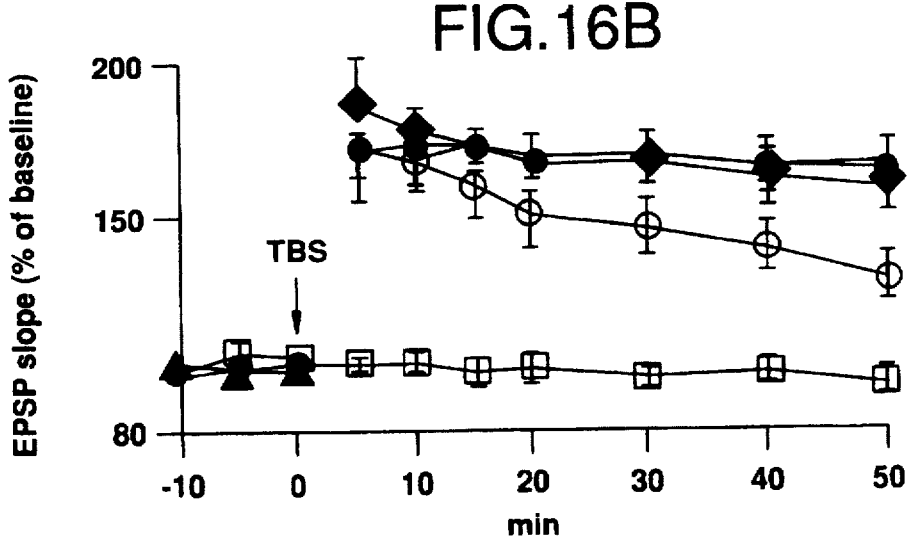
Figure 16C:
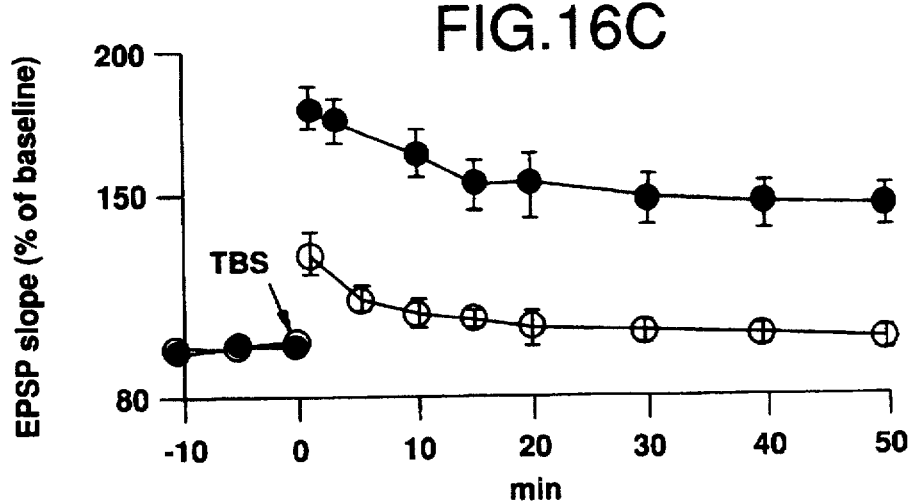

Ig-like domains I-VI and FN type III homologous repeats I-V of L1 were expressed in bacteria and purified as described (Hynes et al. (1992)). Antibodies to NCAM and axonin-1 were produced as described (Larson et al. (1986) *Science* 232:985-988; Bailey et al. (1992) *Science* 256:645-649). Production of oligomannosidic glycopeptides from ribonuclease B and control glycopeptides from asialofetuin have been described (Larson et al. (1986)). Results are shown in FIG. 16.

NMDA receptor-mediated EPSP's were isolated by applying 30 μM of the non-NMDA blocker 6-cyano-7-nitroquinoxaline-2,3-dione (CNQX; Tocris) starting 20 minutes prior to the application of antibodies or glycopeptides. At the end of each experiment, it was verified that D(−)-2-amino-5-phosphonopentanoic acid (D-AP5; 30 μM; Tocris) completely suppressed these responses. Results are shown in FIG. 17.

EXAMPLE 16
L1 exerts neuropreservative effect

An experiment was performed to further elucidate the activity of L1 with CNS nerve tissue. Specifically, aliquot samples of mouse mesencephalon cells were plated and cultured on four separate plates having media prepared as follows: the first control plate was coated with poly-L-lysine alone; a second plate was coated with poly-L-lysine and L1; a third control plate was coated with poly-L-lysine and laminin; and a fourth plate was coated with poly-L-lysine, laminin and L1. All plates received aliquot amounts of cells and were incubated under identical conditions. After 7 days, the plates were all stained for the presence of dopamine and thereafter observed. The plates that were coated with L1 exhibited a growth of 200% to 400% greater than the controls. The plates coated with laminin exhibited greater neurite outgrowth, but not more cells than those coated with L1. The results demonstrate and suggest that L1 exerts a profound neuropreservative effect, as cell viability measured by numbers of cells grown was dramatically increased over controls.

EXAMPLE 17
Soluble L1 (L1-Fc) is functionally active and is a potent agent in neuronal survival Soluble L1 was made in COS cells as a recombinant L1-Fc fusion protein by the procedure described in *Neuron* 14:57-66, 1995. The recombinant protein was purified by Protein A affinity chromatography, and was used either as a substrate coated onto plastic or as a soluble molecule added to the culture medium at approximately 1-10 μg/ml. Neurite outgrowth and survival of mesencephalic neurons from day 17 rat embryos were examined in culture after 7 days in vitro maintenance. Dopaminergic neurons were recognized by immunostaining for dopamine-β-hydroxylase (DBH) and quantified using IBAS morphometric equipment. Cultures with added soluble L1-Fc were maintained on poly-DL-ornithine (PORN) and substrate-coated L1-Fc was added on top of previously coated PORN (under conditions described in Appel et al, *J. Neuroscience* 13:4764-4775, 1993). NCAM-Fc was used as a control.

TABLE

Survival and neurite outgrowth of DBH$^+$ neurons after 7 days in vitro

|  | number of neurons$^+$ | length of neurites$^{++}$ |
|---|---|---|
| substrate-coated L1 | 129 ± 20 | 179 ± 40 |
| soluble L1 | 98 ± 7 | 135 ± 27 |
| PORN only (control) | 14 ± 2 | 37 ± 9 |

Mean values are from at least three independent experiments ± SEM
$^+$The numbers are from a unit field
$^{++}$The lengths of all neurites (total neurite length) per neuron was determined (in μm)

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for promoting neural growth in vivo in the central nervous system of a mammal comprising administering to the central nervous system of said mammal a neural growth promoting amount of an agent, said agent comprising a soluble neural cell adhesion molecule, a fragment thereof, or a Fc-fusion thereof, said molecule selected from a group consisting of L1, L1-CAM, NILE, Nr-CAM, and Ng-CAM, wherein said molecule, said fragment thereof, or Fc-fusion thereof overcomes inhibitory molecular cues found in the central nervous system, and promotes said growth.

2. The method of claim 1 wherein said agents is L1.

3. A method according to claim 1, wherein said agent is L1-Fc.

* * * * *